United States Patent
Satoh et al.

(10) Patent No.: US 8,394,028 B2
(45) Date of Patent: Mar. 12, 2013

(54) ULTRASONIC DIAGNOSTIC APPARATUS AND ULTRASONIC PROBE

(75) Inventors: Yoshiaki Satoh, Kaisei-machi (JP); Hiroyuki Karasawa, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 329 days.

(21) Appl. No.: 12/656,354

(22) Filed: Jan. 27, 2010

(65) Prior Publication Data

US 2010/0191121 A1   Jul. 29, 2010

(30) Foreign Application Priority Data

Jan. 28, 2009  (JP) .................................. 2009-016639
Mar. 27, 2009  (JP) .................................. 2009-079313

(51) Int. Cl.
*A61B 8/14* (2006.01)
(52) U.S. Cl. .................... 600/459; 600/407; 600/437
(58) Field of Classification Search .......... 600/407, 600/437, 443–447
See application file for complete search history.

(56) References Cited

U.S. PATENT DOCUMENTS

| 2003/0181813 A1* | 9/2003 | Ogawa ........................ 600/443 |
| 2008/0097205 A1* | 4/2008 | Takimoto et al. ............. 600/437 |
| 2008/0114247 A1* | 5/2008 | Urbano et al. ................ 600/447 |
| 2009/0040340 A1* | 2/2009 | Nakase et al. ............... 348/231.3 |

FOREIGN PATENT DOCUMENTS

| JP | 2007-243977 A | 9/2007 |
| JP | 2007-275087 | 10/2007 |
| JP | 2008-061938 | 3/2008 |
| JP | 2008-253500 A | 10/2008 |
| JP | 2008-271150 A | 11/2008 |

* cited by examiner

*Primary Examiner* — Tse Chen
*Assistant Examiner* — Joel F Brutus
(74) *Attorney, Agent, or Firm* — Jean C. Edwards, Esq.; Edwards Neils PLLC

(57) ABSTRACT

When a transfer signal according to ultrasonic echoes is wirelessly transmitted from an ultrasonic probe to an ultrasonic diagnostic apparatus main body, the main body and the probe are reliably connected without false recognition. An ultrasonic diagnostic apparatus includes an ultrasonic probe and an ultrasonic diagnostic apparatus main body, and the ultrasonic probe includes a probe ID transport unit having a transport distance shorter than that of a first wireless communication unit for transporting a probe ID for identification of itself in contact or noncontact to an outside, the ultrasonic diagnostic apparatus main body includes a probe ID acquiring unit for acquiring the probe ID transported from the probe ID transport unit, and a second wireless communication unit receives the transfer signal from the ultrasonic probe having the probe ID acquired by the probe ID acquiring unit.

21 Claims, 14 Drawing Sheets

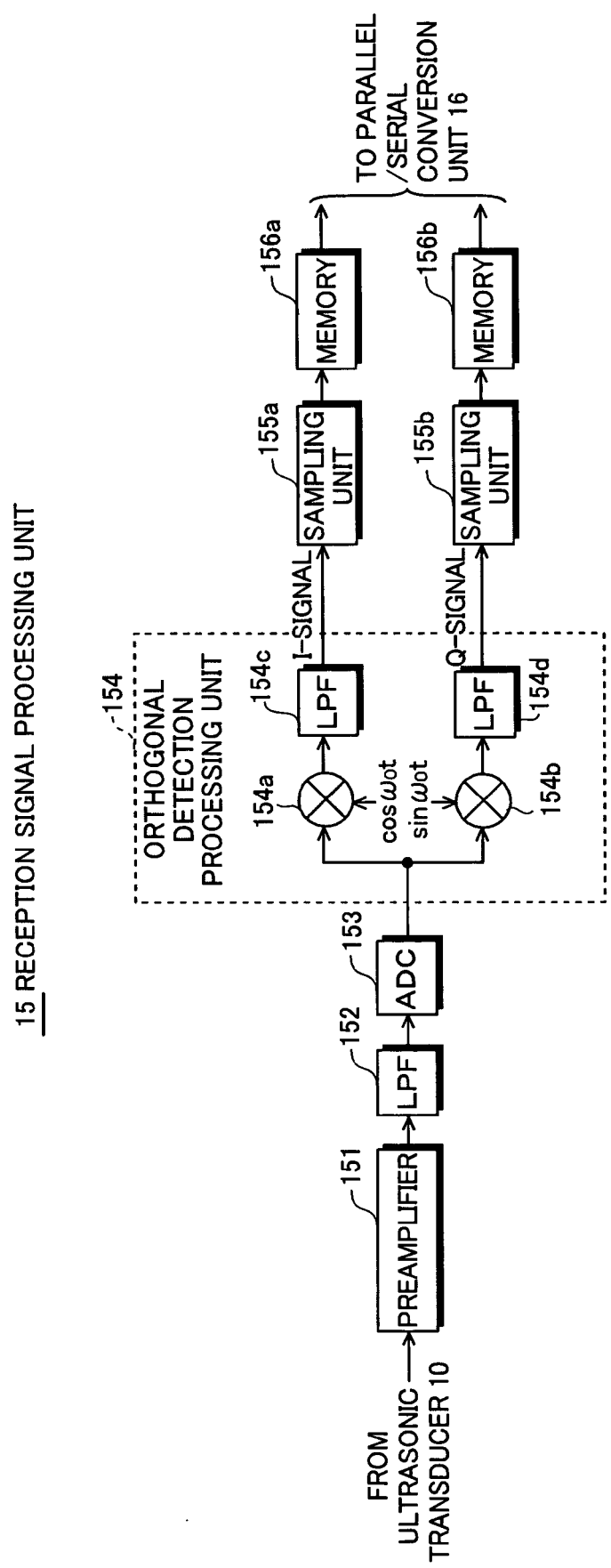

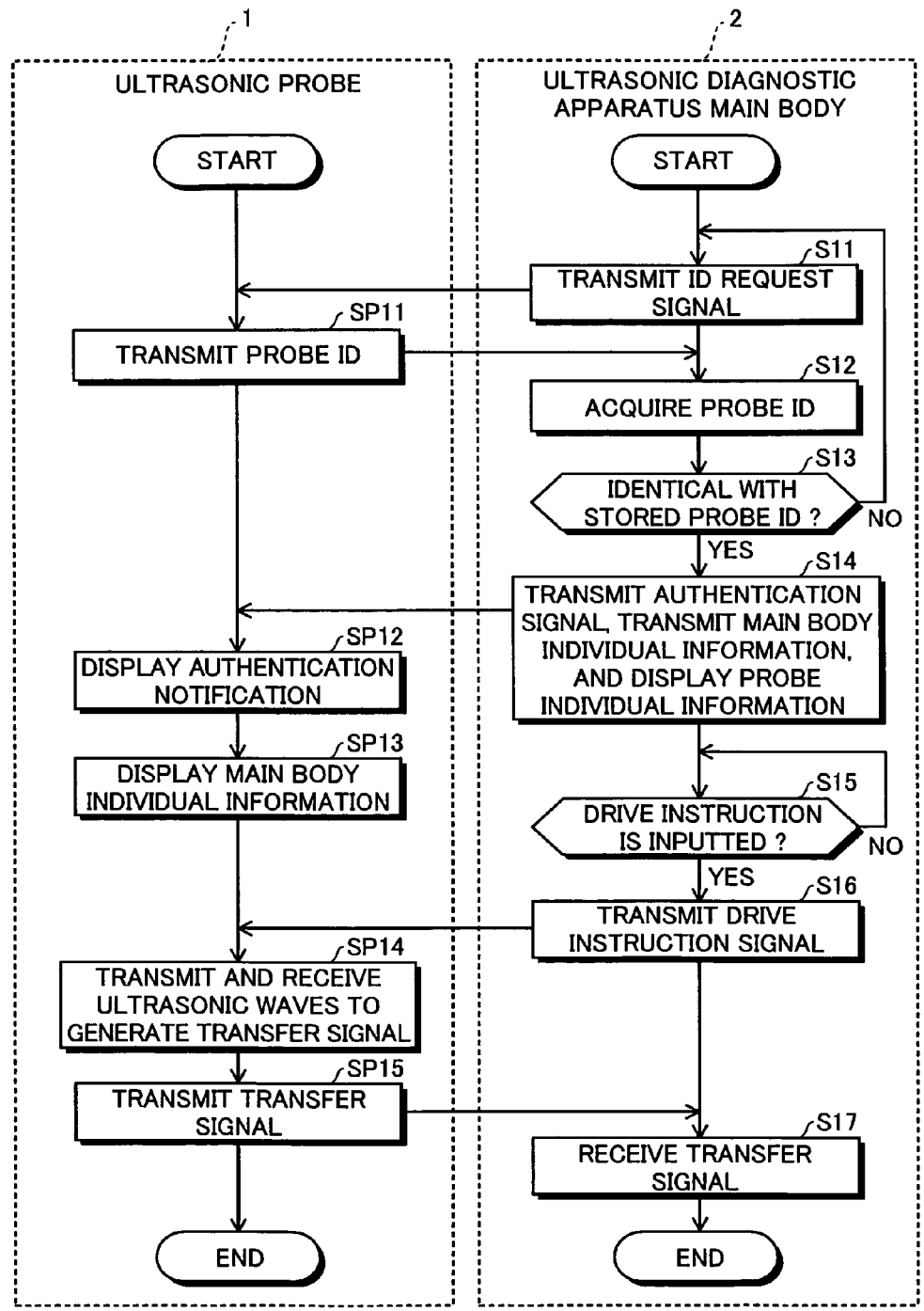

FIG.6A

| PROBE TYPE | SERIAL NUMBER |
|---|---|
| C5-2 | 012324 |

FIG.6B

| MAIN BODY TYPE | SERIAL NUMBER |
|---|---|
| A-100 | 98765 |

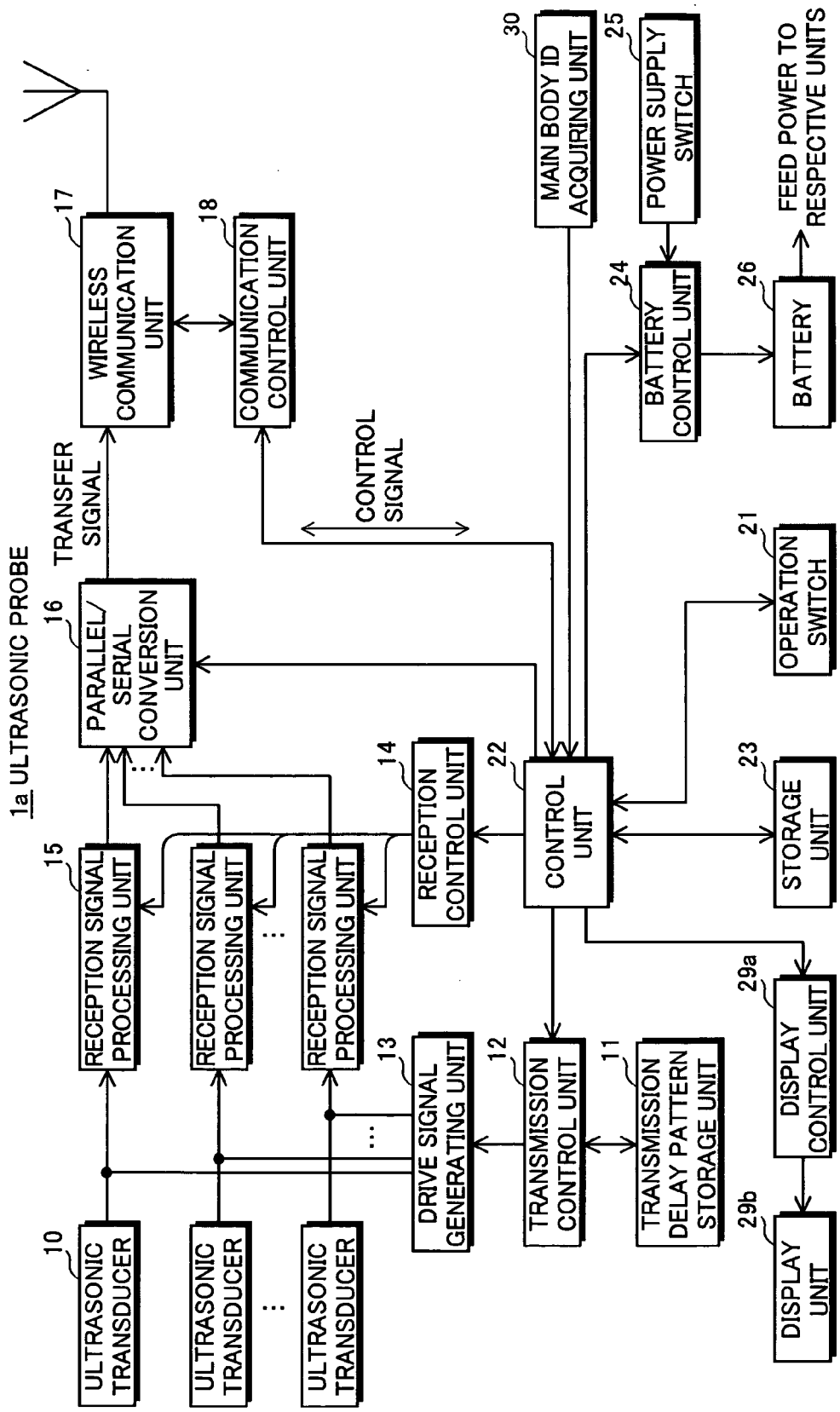

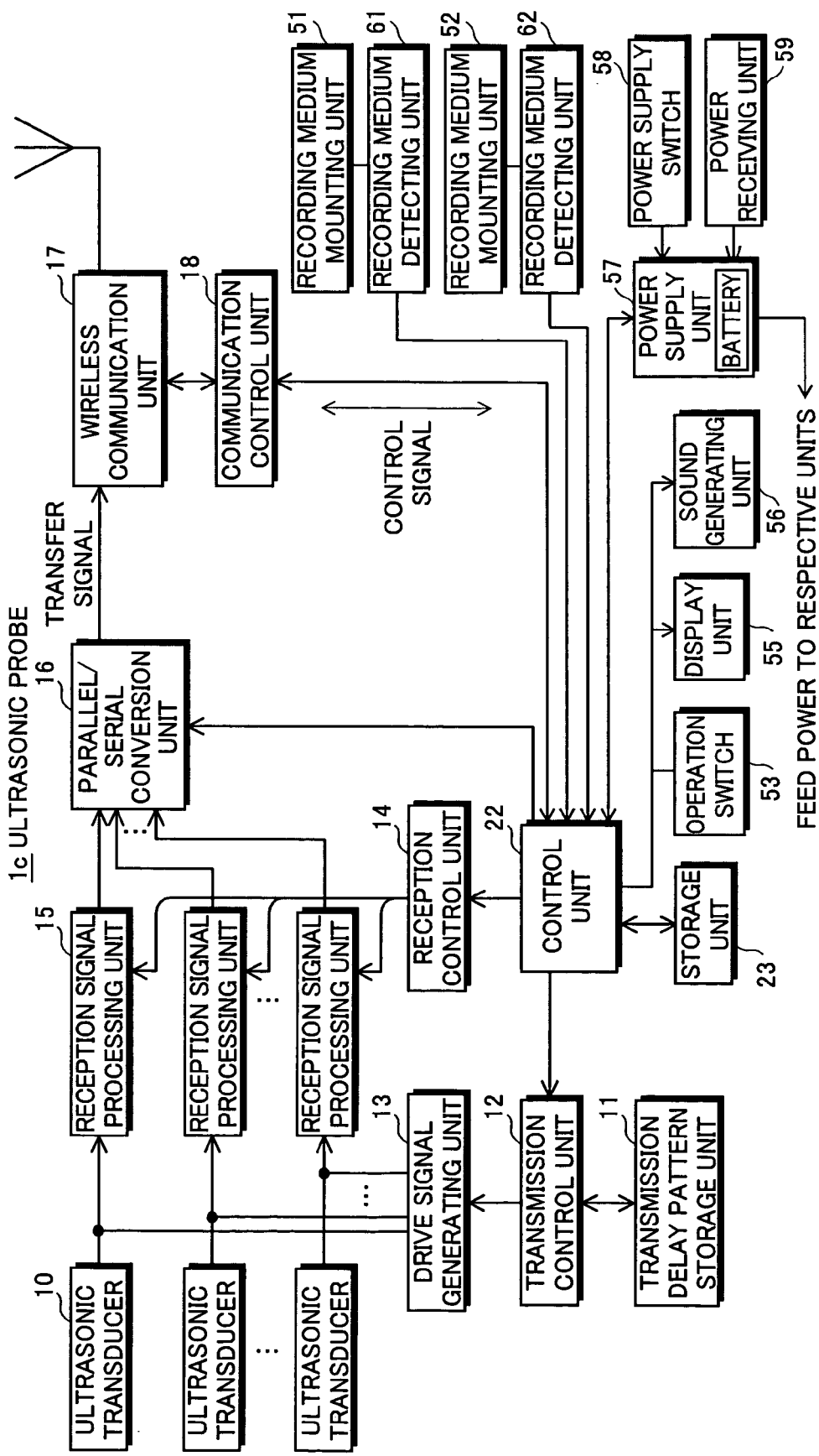

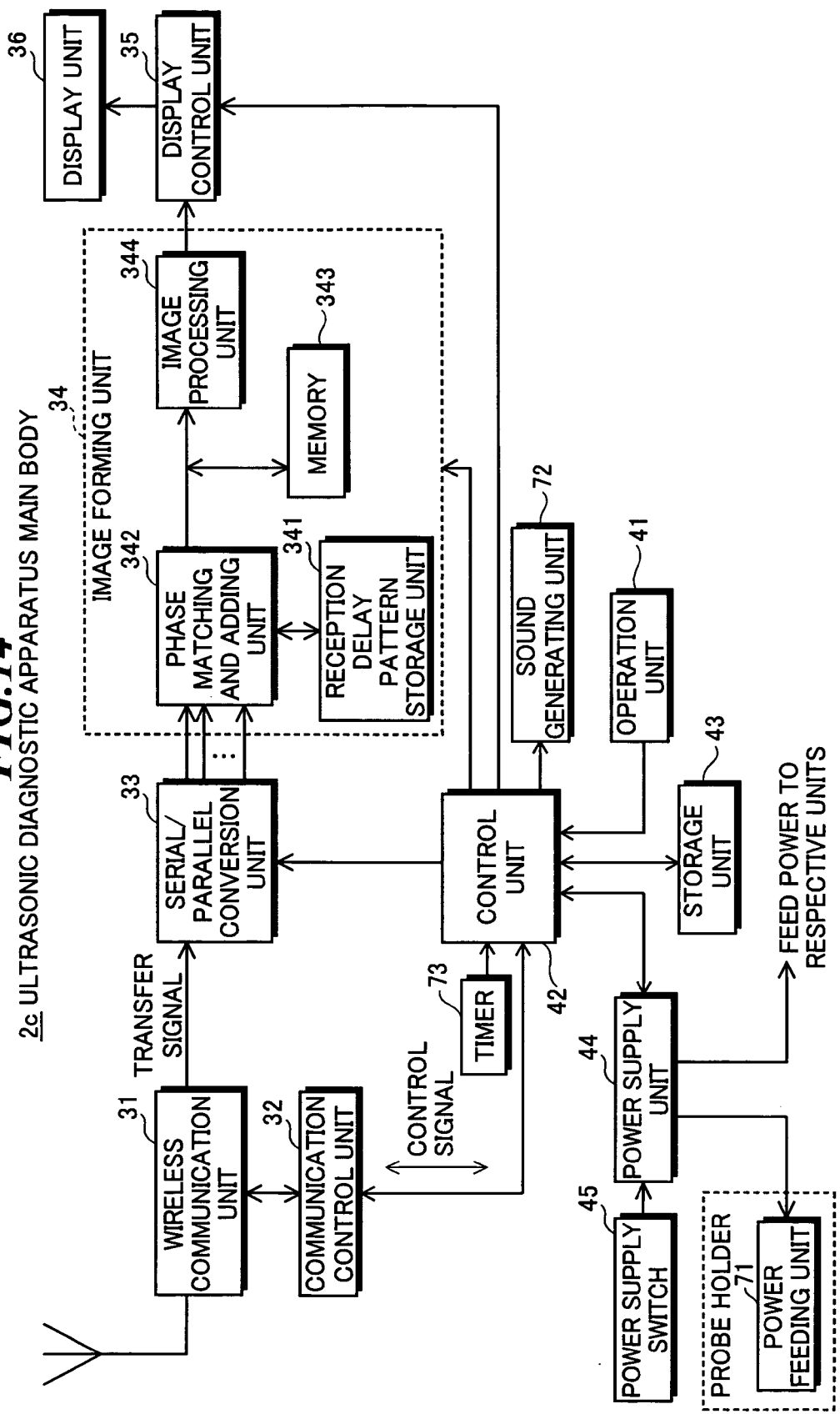

ULTRASONIC DIAGNOSTIC APPARATUS AND ULTRASONIC PROBE

CROSS-REFERENCE TO RELATED APPLICATION

The present application claims priority from Japanese Patent Applications No. 2009-016639 filed on Jan. 28, 2009 and No. 2009-079313 filed on Mar. 27, 2009, the contents of which are incorporated herein by reference in their entirety.

BACKGROUND OF THE INVENTION

1. Field of the Invention

The present invention relates to an ultrasonic diagnostic apparatus in which an ultrasonic probe transmits a signal, which is obtained by transmitting and receiving ultrasonic waves and thereby imaging organs and so on within a living body, to an ultrasonic diagnostic apparatus main body via wireless communication. Further, the present invention relates to an ultrasonic probe to be used in such an ultrasonic diagnostic apparatus.

2. Description of a Related Art

In medical fields, various imaging technologies have been developed for observation and diagnoses within an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics, but also gynecology, circulatory system, digestive system, and so on.

The principle of ultrasonic imaging is as follows. Ultrasonic waves are reflected at a boundary between regions having different acoustic impedances like a boundary between structures within the object. Therefore, by transmitting ultrasonic beams into the object such as a human body and receiving ultrasonic echoes generated within the object, and obtaining reflection points, where the ultrasonic echoes are generated, and reflection intensity, outlines of structures (e.g., internal organs, diseased tissues, and so on) existing within the object can be extracted.

Generally, in an ultrasonic diagnostic apparatus, an ultrasonic probe including plural ultrasonic transducers (vibrators) having transmitting and receiving functions of ultrasonic waves is used. The ultrasonic probe and an ultrasonic diagnostic apparatus main body are often connected via a cable. However, in order to remove the burden of using the cable, ultrasonic diagnostic apparatuses of a wireless communication type for performing wireless information communication between the ultrasonic probe and the ultrasonic diagnostic apparatus main body are being developed. In the ultrasonic diagnostic apparatuses of a wireless communication type, reception condition of a radio signal varies depending on arrangement situations of the ultrasonic probe and the ultrasonic diagnostic apparatus main body.

As a related technology, Japanese Patent Application Publication JP-P2007-275087A discloses an ultrasonic diagnostic apparatus for establishing wireless connection between an ultrasonic diagnostic apparatus main body and a specific ultrasonic probe by wirelessly transmitting probe identification information from an ultrasonic probe to the ultrasonic diagnostic apparatus main body so that the ultrasonic diagnostic apparatus main body identifies the ultrasonic probe corresponding to the probe identification information.

However, in the case where there are plural connectable ultrasonic probes and plural ultrasonic diagnostic apparatus main bodies in a range where wireless communication is enabled, an operation for setting or the like is complicated in order to reliably establish wireless communication between a specific ultrasonic probe and a specific ultrasonic diagnostic apparatus main body to be used, and there is a danger of improper connection when an error occurs in the operation. Further, in the case where wireless communication condition is poor, false recognition of the ultrasonic probe may occur at establishment of wireless communication. In this case, a different kind of control is made by the ultrasonic diagnostic apparatus main body and an abnormal movement may occur, and therefore, there is a possibility that a problem such as a defective image may occur.

By the way, in the ultrasonic diagnostic apparatus, there is a request for forcible management of availability of connection between an ultrasonic probe and an ultrasonic diagnostic apparatus main body in order to prevent, for example, unwanted infection caused when an ultrasonic probe, which was used by one operator and requires sterilization treatment, is carelessly used by another operator.

As a related technology, Japanese Patent Application Publication JP-P2008-61938A discloses a technology for managing a condition of an ultrasonic probe when the ultrasonic probe is disconnected from an ultrasonic diagnostic apparatus main body and not used. The ultrasonic probe includes a handle part for transmitting and receiving ultrasonic waves, a connector connected to the ultrasonic diagnostic apparatus main body, for mediating supply of power and transmission and reception of signals for ultrasonic diagnoses, an internal power supply capable of supplying power to the inside when the connector is detached from the ultrasonic diagnostic apparatus main body, and condition managing means supplied with power from the internal power supply, for managing a condition of the ultrasonic probe.

The ultrasonic probe disclosed in JP-P2008-61938A has a function of managing the condition of the ultrasonic probe when not used, and notifying an operator of the condition. However, an operation for sequentially detecting the condition of the ultrasonic probe is necessary, and attention should be given to reduction in the remaining power of the internal power supply.

SUMMARY OF THE INVENTION

The present invention has been achieved in view of the above-mentioned problems. A first purpose of the present invention is to provide an ultrasonic diagnostic apparatus that can reduce the possibility of false recognition and more reliably establish connection between an ultrasonic diagnostic apparatus main body and an ultrasonic probe when a transfer signal obtained based on ultrasonic echoes is wirelessly transmitted from the probe to the main body. Further, a second purpose of the present invention is to provide an ultrasonic probe that can manage availability of connection between the ultrasonic probe and an ultrasonic diagnostic apparatus main body without wasting an internal power supply of the ultrasonic probe, and an ultrasonic diagnostic apparatus using the ultrasonic probe.

In order to accomplish the above-mentioned purposes, an ultrasonic diagnostic apparatus according to a first aspect of the present invention includes: (i) an ultrasonic probe including plural ultrasonic transducers for transmitting ultrasonic waves according to drive signals, and receiving ultrasonic echoes to output reception signals, a signal processing unit for performing signal processing on the reception signals outputted from the plural ultrasonic transducers to generate a transfer signal, and a first wireless communication unit for transmitting the transfer signal to an outside via wireless communication; and (ii) an ultrasonic diagnostic apparatus main body including a second wireless communication unit for receiving the transfer signal transmitted from the first wireless communication unit, and an image signal generating unit for generating an image signal based on the transfer signal received by the second wireless communication unit; wherein the ultrasonic probe further includes a probe ID transport unit having a transport distance shorter than that of the first wireless communication unit, for transporting a probe ID for identifying the ultrasonic probe to an outside in a contact manner or a noncontact manner; the ultrasonic diagnostic apparatus main body further includes a probe ID acquiring unit for acquiring the probe ID transported from the probe ID transport unit; and the second wireless communication unit receives the transfer signal from an ultrasonic probe having the probe ID acquired by the probe ID acquiring unit.

Further, an ultrasonic probe according to a second aspect of the present invention includes: plural ultrasonic transducers for transmitting ultrasonic waves according to drive signals, and receiving ultrasonic echoes to output reception signals; a signal processing unit for performing signal processing on the reception signals outputted from the plural ultrasonic transducers to generate a transfer signal; a wireless communication unit for transmitting the transfer signal generated by the signal processing unit to an outside via wireless communication; a recording medium mounting unit for mounting a recording medium in which ID information of an examinee or an operator has been recorded; a recording medium detecting unit for detecting mounting of the recording medium on the recording medium mounting unit; a power supply unit including a battery, for supplying power to respective units requiring power; and a control unit for controlling the power supply unit to start power supply based on a detection result of the recording medium detecting unit.

Furthermore, an ultrasonic diagnostic apparatus according to the second aspect of the present invention includes the ultrasonic probe according to the second aspect of the present invention and an ultrasonic diagnostic apparatus main body for performing wireless communication with the ultrasonic probe to control the ultrasonic probe.

According to the first aspect of the present invention, the ultrasonic probe includes the probe ID transport unit having the transport distance shorter than that of the first wireless communication unit, for transporting the probe ID for identifying the ultrasonic probe to the outside in a contact manner or a noncontact manner, and the ultrasonic diagnostic apparatus main body acquires the probe ID transported from the probe ID transport unit and receives the transfer signal from an ultrasonic probe having the acquired probe ID. Therefore, wireless connection can be reliably established between the ultrasonic probe and the ultrasonic diagnostic apparatus main body by using the first and second wireless communication units after the ultrasonic probe is reliably recognized by using the probe ID transported from the probe ID transport unit, and thus, concern about false recognition can be reduced and the ultrasonic probe and the ultrasonic diagnostic apparatus main body can be appropriately connected. Further, the same advantages can be obtained by the ultrasonic probe acquiring the main body ID for identifying the ultrasonic diagnostic apparatus main body instead of the ultrasonic diagnostic apparatus main body acquiring the probe ID for identifying the ultrasonic probe.

Furthermore, according to the second aspect of the present invention, the power supply is started when the mounting of the recording medium on the recording medium mounting unit of the ultrasonic probe is detected, and thereby, the availability of connection between the ultrasonic probe and the ultrasonic diagnostic apparatus main body can be managed without wasting the internal power supply of the ultrasonic probe.

BRIEF DESCRIPTION OF THE DRAWINGS

FIG. 4 shows a configuration example of a reception signal processing unit as shown in FIG. 2;

FIG. 5 is a flowchart for explanation of an operation example of the ultrasonic diagnostic apparatus according to the first embodiment of the present invention;

FIG. 6A shows a display example of probe individual information, and FIG. 6B shows a display example of main body individual information;

FIG. 7 is a block diagram showing a configuration of an ultrasonic probe according to the second embodiment of the present invention;

FIG. 13 is a block diagram showing a configuration of an ultrasonic probe according to the fourth embodiment of the present invention; and FIG. 14 is a block diagram showing a configuration of an ultrasonic diagnostic apparatus main body according to the fourth embodiment of the present invention.

DESCRIPTION OF THE PREFERRED EMBODIMENTS

Hereinafter, embodiments of the present invention will be explained in detail with reference to the drawings. The same signs are assigned to the same component elements and the explanation thereof will be omitted.

Figure 1:
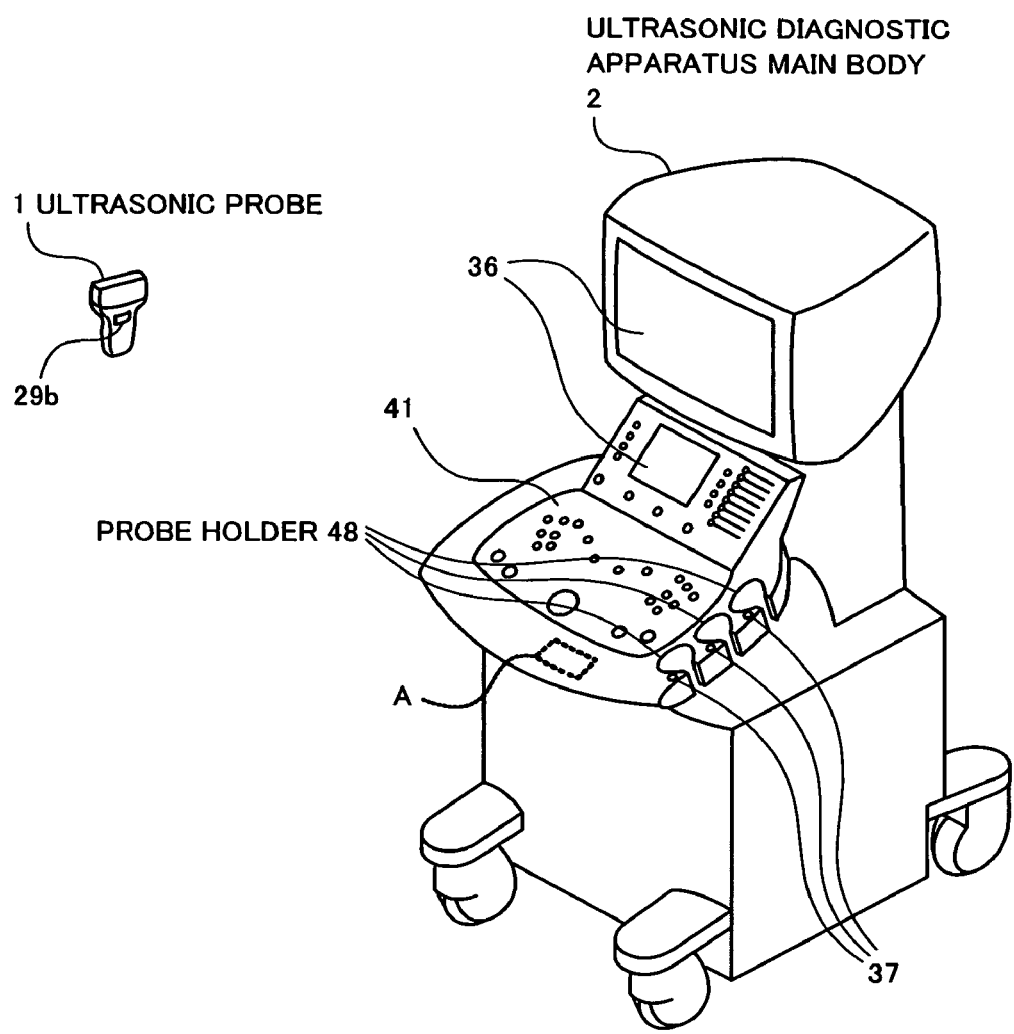
FIG. 1 is a perspective view showing a schematic configuration of an ultrasonic diagnostic apparatus according to embodiments of the present invention.

FIG. 1 is a perspective view showing a schematic configuration of an ultrasonic diagnostic apparatus according to embodiments of the present invention. The ultrasonic diagnostic apparatus according to the embodiments of the present invention includes an ultrasonic probe 1 and an ultrasonic diagnostic apparatus main body 2.

First, an ultrasonic diagnostic apparatus according to the first embodiment of the present invention will be explained.

Figure 2:
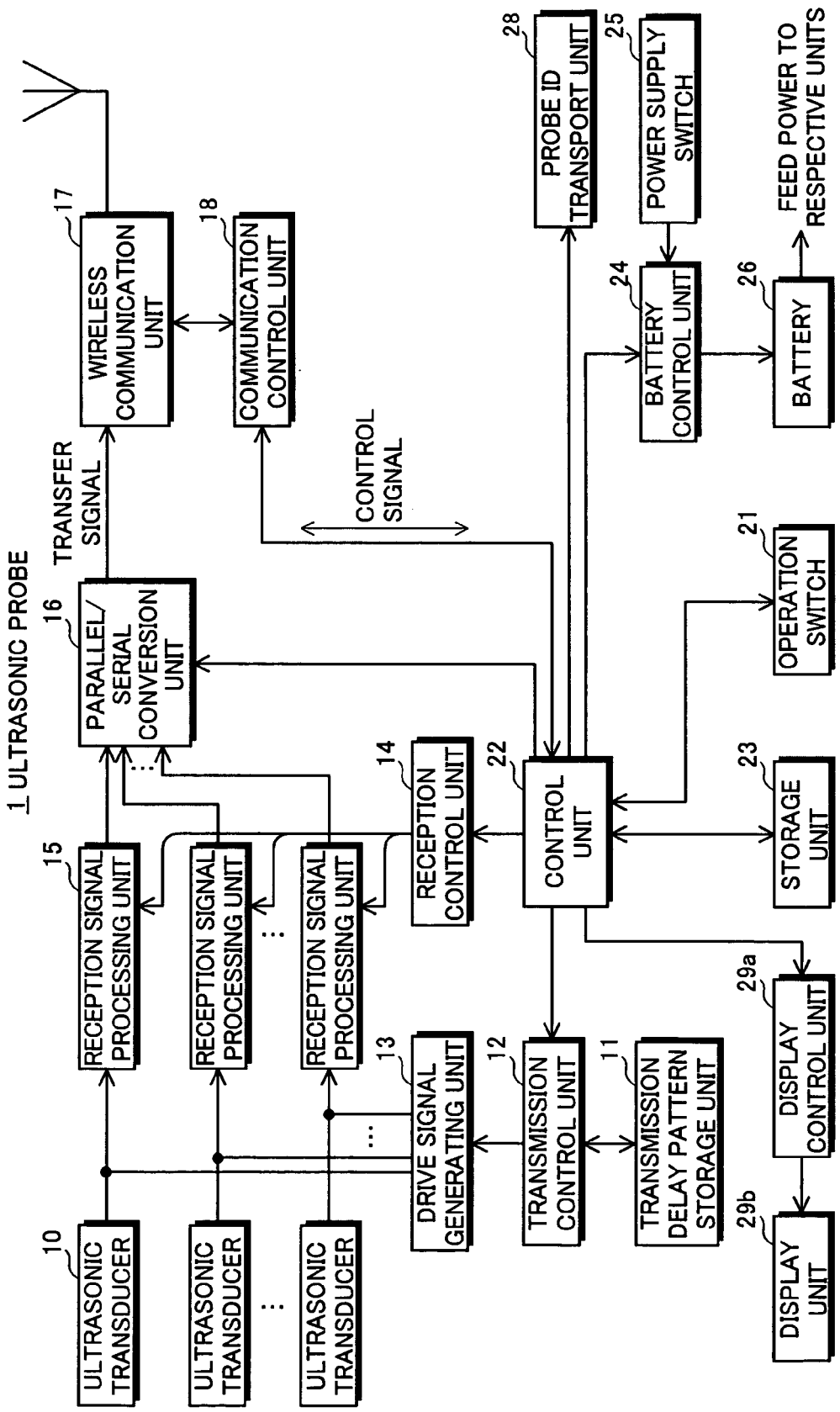
FIG. 2 is a block diagram showing a configuration of an ultrasonic probe according to the first embodiment of the present invention.
Figure 3:
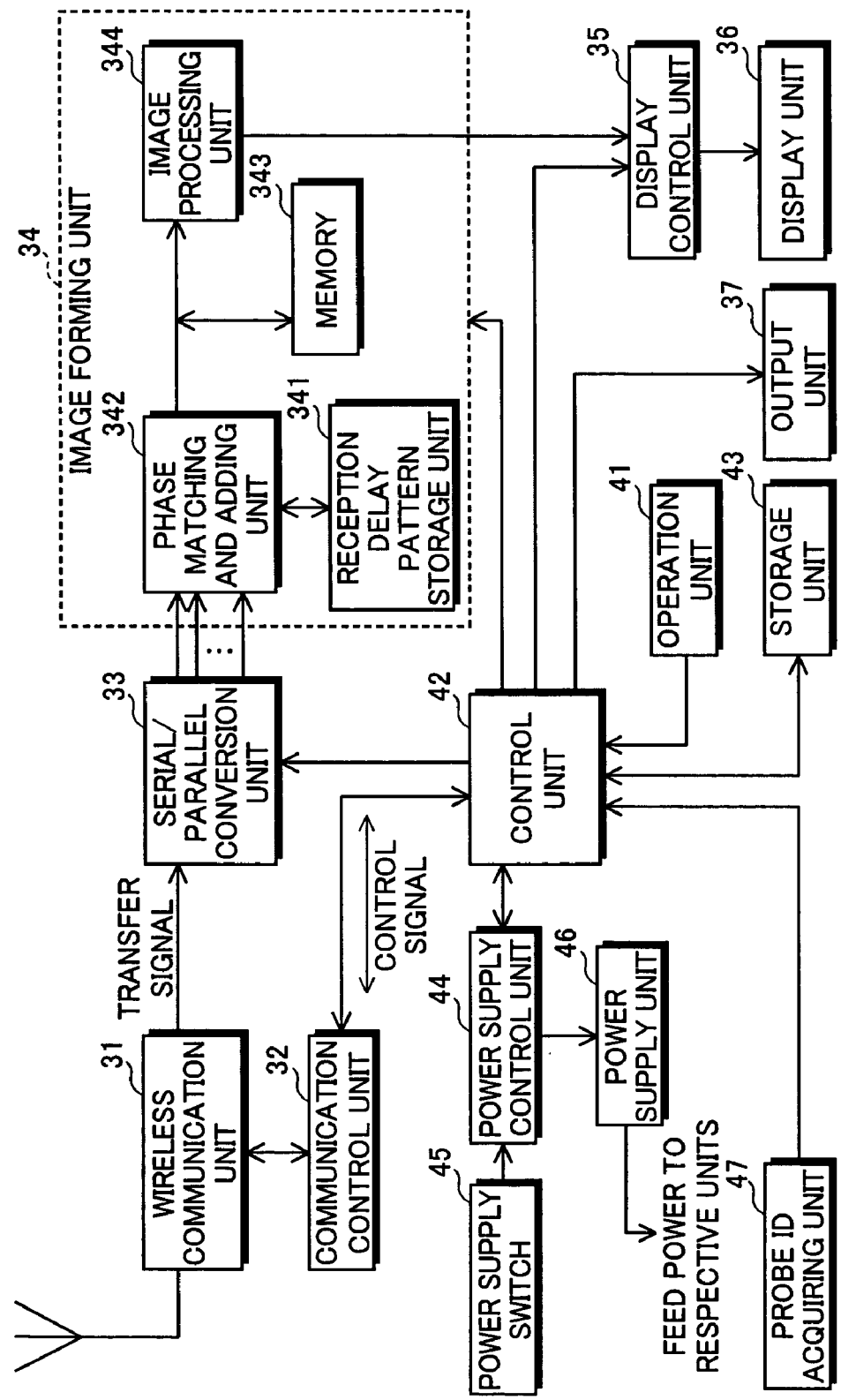
FIG. 3 is a block diagram showing a configuration of an ultrasonic diagnostic apparatus main body according to the first embodiment of the present invention.

FIG. 2 is a block diagram showing a configuration of an ultrasonic probe according to the first embodiment of the present invention, and FIG. 3 is a block diagram showing a configuration of an ultrasonic diagnostic apparatus main body according to the first embodiment of the present invention. The ultrasonic probe 1 may be an external probe of linear-scan type, convex-scan type, sector-scan type, or the like, or an ultrasonic endoscopic probe of radial-scan type or the like.

As shown in FIG. 2, the ultrasonic probe 1 includes plural ultrasonic transducers 10 forming a one-dimensional or two-dimensional transducer array, a transmission delay pattern storage unit 11, a transmission control unit 12, a drive signal generating unit 13, a reception control unit 14, plural channels of reception signal processing units 15, a parallel/serial conversion unit 16, a wireless communication unit 17, a communication control unit 18, an operation switch 21, a control unit 22, a storage unit 23, a battery control unit 24, a power supply switch 25, a battery 26, a probe ID transport unit 28, a display control unit 29a, and a display unit 29b.

Here, the plural reception signal processing units 15 and the parallel/serial conversion unit 16 form a signal processing unit for performing signal processing on reception signals outputted from the plural ultrasonic transducers 10 to generate a transfer signal. The display unit 29b has a function of a probe authentication notification unit for providing a notification of reception of an authentication signal, and a function of a main body information display unit for displaying main body individual information received from the ultrasonic diagnostic apparatus main body.

The plural ultrasonic transducers 10 transmit ultrasonic waves according to applied drive signals, and receive propagating ultrasonic echoes to output reception signals. Each ultrasonic transducer 10 includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like.

When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves and generate electric signals. These electric signals are outputted as reception signals of ultrasonic waves.

The transmission delay pattern storage unit 11 stores plural transmission delay patterns to be used when an ultrasonic beam is formed by using ultrasonic waves transmitted from the plural ultrasonic transducers 10. The transmission control unit 12 selects one transmission delay pattern from among plural transmission delay patterns stored in the transmission delay pattern storage unit 11 according to a transmission direction set by the control unit 22, and sets delay times to be respectively provided to the drive signals of the plural ultrasonic transducers 10 based on the selected transmission delay pattern. Alternatively, the transmission control unit 12 may set delay times such that the ultrasonic waves transmitted at a time from the plural ultrasonic transducers 10 reach the entire imaging region of the object.

The drive signal generating unit 13 includes plural pulsers, for example, and adjusts the amounts of delay of the drive signals based on the transmission delay pattern selected by the transmission control unit 12 and supplies the drive signals to the plural ultrasonic transducers 10 such that the ultrasonic waves transmitted from the plural ultrasonic transducers 10 form an ultrasonic beam, or supplies the drive signals to the plural ultrasonic transducers 10 such that the ultrasonic waves transmitted at a time from the plural ultrasonic transducers 10 reach the entire imaging region of the object.

The reception control unit 14 controls the operation of the plural channels of reception signal processing units 15. Each channel of reception signal processing unit 15 performs orthogonal detection processing or orthogonal sampling processing on the reception signal outputted from the corresponding ultrasonic transducer 10 to generate a complex baseband signal, samples the complex baseband signal to generate sample data, and supplies the sample data to the parallel/serial conversion unit 16.

FIG. 4 shows a configuration example of the reception signal processing unit as shown in FIG. 2. As shown in FIG. 4, each channel of reception signal processing unit 15 includes a preamplifier 151, a low-pass filter (LPF) 152, an analog/digital converter (ADC) 153, an orthogonal detection processing unit 154, sampling units 155a and 155b, and memories 156a and 156b.

The preamplifier 151 amplifies the reception signal (RF signal) outputted from the ultrasonic transducer 10, and the LPF 152 limits a band of the reception signal outputted from the preamplifier 151 to prevent aliasing in A/D conversion. The ADC 153 converts the analog reception signal outputted from the LPF 152 into a digital reception signal.

If serialization of data remaining in the RF signals is performed, the transmission bit rate becomes extremely higher and the communication speed and the operation speed of the memories cannot keep up with the transmission bit rate. On the other hand, if the data is serialized after reception focusing processing, the transmission bit rate can be reduced. However, a circuit for the reception focusing processing is large-scaled and hard to be incorporated into the ultrasonic probe. Accordingly, in the embodiment, orthogonal detection processing or orthogonal sampling processing is performed on the reception signal to drop the frequency range of the reception signal to the baseband frequency range and then the data is serialized, and thereby, the transmission bit rate is reduced.

The orthogonal detection processing unit 154 performs orthogonal detection processing on the reception signal to generate a complex baseband signal (I-signal and Q-signal). As shown in FIG. 4, the orthogonal detection processing unit 154 includes mixers (multiplication circuits) 154a and 154b, and low-pass filters (LPFs) 154c and 154d. The mixer 154a multiplies the reception signal by a local oscillation signal cos $\omega_0 t$, and the LPF 154c performs low-pass filter processing on the signal outputted from the mixer 154a, and thereby, an I-signal representing a real number component is generated. On the other hand, the mixer 154b multiplies the reception signal by a local oscillation signal sin $\omega_0 t$, which is obtained by shifting a phase of the local oscillation signal cos $\omega_0 t$ by $\pi/2$, and the LPF 154d performs low-pass filter processing on the signal outputted from the mixer 154b, and thereby, a Q-signal representing an imaginary number component is generated.

The sampling units 155a and 155b sample (resample) the complex baseband signal (I-signal and Q-signal) generated by the orthogonal detection processing unit 154 to generate two channels of sample data, respectively. The generated two channels of sample data are stored in the memories 156a and 156b, respectively.

Referring to FIG. 2 again, the parallel/serial conversion unit 16 converts the parallel sample data generated by the plural channels of reception signal processing units 15 into serial sample data (a transfer signal). For example, the parallel/serial conversion unit 16 converts 128 channels of parallel data obtained based on the 64 reception signals outputted from the 64 ultrasonic transducers into one channel, or two, three or four channels of serial sample data. Thereby, compared to the number of ultrasonic transducers 10, the number of transmission channels is significantly reduced.

The wireless communication unit 17 modulates a carrier signal based on the transfer signal to generate a transmission signal and supplies the transmission signal to an antenna to transmit electric waves from the antenna, and thereby, transmits a transfer signal. As a modulation system, for example, ASK (amplitude shift keying), PSK (phase shift keying), QPSK (quadrature phase shift keying), 16QAM (16 quadrature amplitude modulation), or the like is used. In the case of using the ASK or the PSK, one channel of serial data can be transmitted in one route, in the case of using the QPSK, two channels of serial data can be transmitted in one route, and in the case of using the 16QAM, four channels of serial data can be transmitted in one route.

In this manner, the wireless communication unit 17 performs wireless communication with the ultrasonic diagnostic apparatus main body 2, and thereby, transmits the transfer signal to the ultrasonic diagnostic apparatus main body 2, and receives an authentication signal and various kinds of control signals transmitted from the ultrasonic diagnostic apparatus main body 2 to output the received signals to the communication control unit 18. The communication control unit 18 controls the wireless communication unit 17 to transmit the transfer signal, and outputs the authentication signal and the various kinds of control signals received by the wireless communication unit 17 to the control unit 22. The control unit 22 controls the respective units of the ultrasonic probe 1 according to the various kinds of control signals transmitted from the ultrasonic diagnostic apparatus main body 2.

The storage unit 23 stores a probe ID unique to the ultrasonic probe 1, and the probe ID is readable by the control unit 22. The probe ID is information for individual identification of the ultrasonic probe 1, and includes, for example, information representing the manufacturer of the probe, information representing the type of the probe, information corresponding to a serial number, and so on. In order to distinguish the ultrasonic probe by using the probe ID, according to need, information as to the type or the like representing common applicable specifications may be sufficient, or information strictly distinguishing an individual ultrasonic probe may be used when the ultrasonic probe is adjusted for special specifications.

The probe ID transport unit 28 receives the probe ID from the control unit 22 prior to ultrasonic imaging in order to decide the combination of the ultrasonic probe 1 and the ultrasonic diagnostic apparatus main body 2, and generates a transmission signal for the probe ID based thereon and supplies the transmission signal to an antenna to transmit electric waves from the antenna, and thereby, transmits the probe ID. The probe ID transport unit 28 is formed to have a transport distance of the transmission signal shorter than that of the wireless communication unit 17. For example, when the probe ID transport unit 28 is formed by a wireless transmitter as in the above-mentioned example, the transmission electric wave intensity of the probe ID transport unit 28 is set to a value weaker than that of the wireless communication unit 17. Alternatively, the probe ID transport unit 28 may be formed by printing a barcode or the like, and the probe ID may be read by an optical reading device. Further, transport means for RFID, infrared communication, or the like may be used as the probe ID transport unit 28.

The operation switch 21 includes a switch for setting the ultrasonic diagnostic apparatus in a live mode or a freeze mode. Here, the live mode is a mode of displaying a moving image based on the reception signals sequentially obtained by transmitting and receiving ultrasonic waves, and the freeze mode is a mode of displaying a still image based on the reception signals or sound ray signals stored in the memory or the like. The setting signal for setting the live mode or the freeze mode is included in the transmission signal together with the transfer signal and transmitted to the ultrasonic diagnostic apparatus main body 2. Alternatively, the switching between the live mode and the freeze mode may be performed in the ultrasonic diagnostic apparatus main body 2.

The battery 26 supplies power to the respective units requiring power such as the drive signal generating unit 13, the reception signal processing units 15, the parallel/serial conversion unit 16, the wireless communication unit 17, the control unit 22, and so on. The ultrasonic probe 1 is provided with the power supply switch 25, and the battery control unit 24 controls whether or not the power is supplied from the battery 26 to the respective units according to the status of the power supply switch 25.

In addition, even in the ultrasonic probe employing the wireless communication system, electric power may be supplied via a wire. In the case where electric power is supplied by using an electric wire, the operation of the ultrasonic probe 1 may be restricted in some degree because the ultrasonic probe 1 is constricted by the length of the electric wire or entanglement of the electric wire should be prevented. However, the battery 26, the battery control unit 24, and so on may be omitted or simplified, and thus, the ultrasonic probe 1 can be made smaller and lighter and the usability can be improved.

When the wireless communication unit 17 receives the authentication signal and the main body individual information, which will be described later, from the ultrasonic diagnostic apparatus main body 2, the display control unit 29*a* allows the display unit 29*b* to display the authentication notification and the main body individual information according to the control signals of the control unit 22. The display unit 29*b* includes a lighting device such as an LED or a display device such as an LCD, and displays the authentication notification and the main body individual information under the control of the display control unit 29*a*. In addition, the authentication notification is not limited to the display using the display unit 29*b*, but may be performed by sound, vibration, or the like.

In the above-mentioned configuration, the transmission control unit 12, the reception control unit 14, the orthogonal detection processing unit 154 (FIG. 4), the sampling units 155*a* and 155*b* (FIG. 4), the parallel/serial conversion unit 16, the communication control unit 18, the control unit 22, the battery control unit 24, and the display control unit 29*a* may be formed of digital circuits, or formed of a CPU and software (program) for allowing the CPU to perform various kinds of processing. The software (program) is stored in the storage unit 23. Alternatively, the orthogonal detection processing unit 154 may be formed of an analog circuit. In this case, the ADC 153 is omitted, and A/D conversion of the complex baseband signal is performed by the sampling units 155*a* and 155*b*.

On the other hand, referring to FIG. 3, the ultrasonic diagnostic apparatus main body 2 includes a wireless communication unit 31, a communication control unit 32, a serial/ parallel conversion unit 33, an image forming unit 34, a display control unit 35, a display unit 36, an operation unit 41, a control unit 42, a storage unit 43, a power supply control unit 44, a power supply switch 45, a power supply unit 46, and a probe ID acquiring unit 47.

Here, the serial/parallel conversion unit 33 and the image forming unit 34 form an image signal generating unit for generating an image signal based on the transfer signal received by the wireless communication unit 31. The storage unit 43 has a function of a probe ID storage unit for storing plural probe IDs. The control unit 42 has a function of a probe authentication unit for generating an authentication signal in the case where the probe ID acquired by the probe ID acquiring unit is identical with one of the plural probe IDs stored in the probe ID storage unit. The display unit 36 has a function of a probe information display unit for displaying probe individual information of the ultrasonic probe having the probe ID acquired by the probe ID acquiring unit.

The wireless communication unit 31 performs wireless communication with the wireless communication unit 17 of the ultrasonic probe 1 to receive the transfer signal transmitted from the ultrasonic probe 1. Further, the wireless communication unit 31 transmits the authentication signal, the main body individual information, and various kinds of control signals including a drive instruction signal, which will be described later, to the ultrasonic probe 1. The wireless communication unit 31 demodulates the signal received by an antenna to output serial sample data (transfer signal) representing the complex baseband signals obtained from the reception signals outputted from the plural ultrasonic transducers.

The communication control unit 32 controls the wireless communication unit 31 to transmit the authentication signal, the main body individual information, and various kinds of control signals under the control of the control unit 42. The serial/parallel conversion unit 33 converts the serial sample data outputted from the wireless communication unit 31 into parallel sample data corresponding to the plural ultrasonic transducers.

The image forming unit 34 generates an ultrasonic image signal representing image information on tissues within the object based on the parallel sample data outputted from the serial/parallel conversion unit 33. The image forming unit 34 includes a reception delay pattern storage unit 341, a phase matching and adding unit 342, a memory 343, and an image processing unit 344.

The reception delay pattern storage unit 341 stores plural reception delay patterns to be used when reception focusing processing is performed on the complex baseband signals obtained from the reception signals outputted from the plural ultrasonic transducers. The phase matching and adding unit 342 selects one reception delay pattern from the plural reception delay patterns stored in the reception delay pattern storage unit 341 according to the reception direction set in the control unit 42, and performs reception focusing processing by providing delays to the plural complex baseband signals based on the selected reception delay pattern and adding the plural complex baseband signals to one another. By the reception focusing processing, baseband signals (sound ray signals), in which the focus of the ultrasonic echoes is narrowed, are formed.

The memory 343 sequentially stores the sound ray signals generated by the phase matching and adding unit 342. The image processing unit 344 generates the ultrasonic image signal representing image information on tissues within the object based on the sound ray signals generated by the phase matching and adding unit 342 in the live mode and based on the sound ray signals stored in the memory 343 in the freeze mode.

The ultrasonic diagnostic apparatus according to the embodiment may execute ultrasonic examinations in a mode selected from a B-mode, a CF (color flow)-mode, a D (Doppler)-mode, and an M-mode. Here, the B-mode refers to a mode of converting amplitudes of ultrasonic echoes into brightness to display a two-dimensional tomographic image, the CF-mode refers to a mode of mapping average blood flow velocities, flow fluctuations, intensity of flow signals, flow power, or the like in various colors to superimpose it on a B-mode image and display the image. Further, the D-mode refers to a mode of detecting motion of an ultrasonic echo source as change of an ultrasonic frequency to display the speed thereof, and the M-mode refers to a mode of continuously capturing a moving ultrasonic echo source to display the track thereof as a waveform.

The image processing unit 344 generates an ultrasonic image signal representing an ultrasonic image in the selected mode. The image processing unit 344 includes an STC (sensitivity time control) part, and a DSC (digital scan converter). The STC part performs attenuation correction by distance according to the depths of the reflection positions of ultrasonic waves on the sound ray signals. The DSC converts (raster-converts) the sound ray signals corrected by the STC part into an image signal that follows the normal scan system of television signals, and performs necessary image processing such as gradation processing to generate an ultrasonic image signal.

The probe ID acquiring unit 47 performs wireless communication with the probe ID transport unit 28 of the ultrasonic probe 1 as shown in FIG. 2 to acquire the probe ID from the ultrasonic probe 1. The configuration of the probe ID acquiring unit 47 is not limited to a wireless receiver, but may be various configurations compliant to the transport system of the probe ID transport unit 28. For example, in the case where the probe ID transport unit 28 is formed by printing a barcode or the like, the probe ID acquiring unit 47 is formed of an optical reading device. Alternatively, receiving means for RFID, infrared communication, or the like may be used as the probe ID acquiring unit 47.

Further, the probe ID acquiring unit 47 is not limited to a noncontact type, but may be a contact type. The probe ID acquiring unit 47 of a contact type may be constructed to acquire an electric signal including the probe ID through an input terminal electrically connectable to an output terminal of the probe ID transport unit 28, or may be constructed to read a shape unique to the ultrasonic probe and formed on a surface of the probe ID transport unit 28 by employing a mechanical sensor or a pressure sensor.

As shown in the above-mentioned example, it is desirable that the probe ID acquiring unit 47 is suitable for reading information from a position extremely close thereto in order to reliably identify the specific ultrasonic probe 1 and the ultrasonic diagnostic apparatus main body 2.

The probe ID acquisition operation may be automatically performed when the power of the ultrasonic diagnostic apparatus main body 2 is turned on, or may be performed by an operation of the operator using the operation unit 41. Further, in the case where the probe ID acquiring unit 47 is provided in the probe holder 48 (see FIG. 1) of the ultrasonic diagnostic apparatus main body 2 and the probe ID acquisition operation is automatically executed by the ultrasonic probe 1 held in the probe holder 48 when the power of the ultrasonic diagnostic apparatus main body 2 is turned on, the operation of the operator for acquiring a new probe ID from the ultrasonic probe 1 held in the probe holder 48 is unnecessary.

In the case where plural probe holders 48 are provided in one ultrasonic diagnostic apparatus main body 2, the plural probe ID acquiring units 47 are respectively provided in the plural probe holders 48. When the plural ultrasonic probes 1 are respectively held in the plural probe holders 48, the probe IDs of the plural ultrasonic probes 1 are acquired. When the probe IDs of the plural ultrasonic probes 1 are acquired, probe individual information of the plural ultrasonic probes 1 are displayed on the display unit 36. Further, output units 37 for notifying the probe ID acquisition statuses may be provided near the respective probe holders 48, and these output units 37 may output indication, sound, vibration, or the like for notifying the acquisition of the probe IDs.

When the probe IDs of the plural ultrasonic probes 1 are acquired, the ultrasonic probe 1 that practically performs communication may be selected based on the operation of the operator using the operation unit 41. Alternatively, when the operator takes out the ultrasonic probe 1 in order to use the ultrasonic probe 1, the probe ID acquiring unit may recognize that the ultrasonic probe 1 has been taken out and establish wireless connection with the taken out probe 1, and thus, the operation of the operator for the probe selection becomes unnecessary. In this case, by automatically disabling the wireless connection when the ultrasonic probe 1 is returned into the probe holder 48, power consumption can be suppressed and, when another ultrasonic probe 1 is used, excessive operation of disabling the wireless connection may be unnecessary.

The locations, where the probe ID acquiring units 47 and the output units 37 are placed, are not limited to plural locations respectively close to the individual probe holders 48, but may be one location as shown by a broken line "A" in FIG. 1. In this case, the acquisition of the probe IDs is individually performed after the operator takes out the ultrasonic probes 1 from the probe holders 48. In order to facilitate operation of causing the ultrasonic diagnostic apparatus main body 2 to recognize the ultrasonic probe 1 taken out from the probe holder 48, it is preferable that the probe ID acquiring unit 47 is provided within an operation panel at the front side along the placement side of the probe holder 48, or in a location apart to the degree that the probe ID of the ultrasonic probe 1 within the probe holder 48 is not acquired and not too much apart from the probe holder 48 in a viewpoint of operation. Specifically, it is desirable that the probe ID acquiring unit 47 is provided in a location at a distance from 5 cm to 30 cm, more desirably, at a distance from 10 cm to 20 cm from the probe holder 48.

The display control unit 35 controls the display unit 36 to display an ultrasonic diagnostic image based on the ultrasonic image signal generated by the image forming unit 34. Further, the display control unit 35 controls the display unit 36 to display the probe individual information based on the probe ID acquired by the probe ID acquiring unit 47. The display unit 36 includes a display device such as an LCD, and displays an ultrasonic diagnostic image and/or the probe individual information under the control of the display control unit 35.

The storage unit 43 stores main body individual information for identifying the ultrasonic diagnostic apparatus main body 2. Further, the storage unit 43 stores the probe IDs of the plural ultrasonic probes 1 acquired by the probe ID acquiring unit 47 or acquired by the input from the operation unit 41.

The control unit 42 controls the respective units of the ultrasonic diagnostic apparatus according to the operation of an operator using the operation unit 41. The power supply switch 45 is provided in the ultrasonic diagnostic apparatus main body 2, and the power supply control unit 44 controls ON/OFF of the power supply unit 46 according to the status of the power supply switch 45.

Further, when the probe ID acquiring unit 47 acquires the probe ID from the ultrasonic probe 1, the control unit 42 compares the probe ID acquired by the probe ID acquiring unit 47 and the probe IDs stored in the storage unit 43. Then, the control unit 42 generates an authentication signal when the probe ID acquired by the probe ID acquiring unit 47 is identical with one of the probe IDs stored in the storage unit 43.

In the above-mentioned configuration, the communication control unit 32, the serial/parallel conversion unit 33, the phase matching and adding unit 342, the image processing unit 344, the display control unit 35, the control unit 42, and the power supply control unit 44 are formed of a CPU and software (programs) for allowing the CPU to perform various kinds of processing. However, they may be formed of digital circuits. The software (programs) is stored in the storage unit 43. As a recording medium in the storage unit 43, not only a built-in hard disk but also a flexible disk, MO, MT, RAM, CD-ROM, DVD-ROM, or the like may be used.

Next, an operation example of the ultrasonic diagnostic apparatus according to the first embodiment of the present invention will be explained by referring to FIGS. 2, 3 and 5. FIG. 5 is a flowchart for explanation of the operation example of the ultrasonic diagnostic apparatus according to the first embodiment of the present invention. In FIG. 5, the operation of the ultrasonic probe on the left side and the operation of the ultrasonic diagnostic apparatus main body on the right side are shown so that the interference relationship with each other is clear. Note that the power supply switch 45 of the ultrasonic diagnostic apparatus main body 2 is assumed to be constantly in "ON" state.

When the operator of the ultrasonic diagnostic apparatus turns on the power supply switch 25 of the ultrasonic probe 1, the ultrasonic probe 1 turns from the deactivated condition to the standby condition (sleep condition). Here, the standby condition is a condition in which the control unit 22 and so on operate at a lower clock frequency than that in the normal operation condition. For example, the control unit 22 and so on operate at a clock frequency of 100 MHz in the normal operation condition, and operate at a clock frequency of 1 MHz in the standby condition. In the standby condition, it is possible to transmit and receive the probe IDs and various kinds of control signals, but it is impossible to transmit and receive the transfer signal. Furthermore, in the standby condition, the operation of the signal system circuits such as the drive signal generating unit 13, the reception signal processing units 15, and the parallel/serial conversion unit 16 may be stopped.

When the ultrasonic probe 1 is in the standby condition, the control unit 42 of the ultrasonic diagnostic apparatus main body 2 controls the communication control unit 32 to transmit an ID request signal for requesting transmission of the probe ID from the wireless communication unit 31 to the ultrasonic probe 1 at step S11.

When the wireless communication unit 17 of the ultrasonic probe 1 receives the ID request signal, in response, the control unit 22 reads out the probe ID unique to the ultrasonic probe 1 from the storage unit 23 and controls the probe ID transport unit 28 to transmit a probe ID signal representing the probe ID at step SP11.

At step S12, the probe ID acquiring unit 47 of the ultrasonic diagnostic apparatus main body 2 receives and demodulates the signal transmitted from the ultrasonic probe 1 to acquire the probe ID, and outputs the probe ID to the control unit 42. At step S13, the control unit 42 compares the probe ID acquired by the probe ID acquiring unit 47 with the probe IDs stored in the storage unit 43, and generates an authentication signal in the case where the probe ID acquired by the probe ID acquiring unit 47 is identical with one of the probe IDs stored in the storage unit 43. In the case where there is no identical probe ID in the storage unit 43, the process returns to step S11, and the wireless communication unit 31 retransmits an ID request signal.

At step S14, the control unit 42 controls the communication control unit 32 to transmit the authentication signal including the probe ID acquired by the probe ID acquiring unit 47 from the wireless communication unit 31. Further, the control unit 42 reads out the main body individual information from the storage unit 43, and controls the communication control unit 32 to transmit the main body individual information from the wireless communication unit 31. Furthermore, the control unit 42 controls the display control unit 35 to allow the display unit 36 to display the authenticated probe ID or the corresponding probe individual information.

FIG. 6A shows a display example of the probe individual information. The probe individual information includes not only the information on the probe type but also information for identifying the ultrasonic probe 1 such as a serial number. Thereby, the operator is able to know with which ultrasonic probe 1 the ultrasonic diagnostic apparatus main body 2 can communicate.

The wireless communication unit 17 of the ultrasonic probe 1 receives the authentication signal and the main body individual information transmitted from the ultrasonic diagnostic apparatus main body 2, and outputs the authentication signal and the main body individual information to the communication control unit 18. The communication control unit 18 detects the authentication signal and the main body individual information and outputs them to the control unit 22. In addition, the control unit 22 may determine whether the probe ID included in the received authentication signal is identical with the probe ID stored in the storage unit 23 and unique to the ultrasonic probe 1. Thereby, it can be confirmed that the probe ID has been correctly transported.

At step SP12, the control unit 22 of the ultrasonic probe 1 allows the display unit 29b, via the display control unit 29a, to display the authentication notification based on the received authentication signal. Thereby, the operator is able to know that the ultrasonic probe 1 can communicate with the ultrasonic diagnostic apparatus main body 2. At step SP13, the control unit 22 allows the display unit 29b, via the display control unit 29a, to display the main body individual information.

FIG. 6B shows a display example of the main body individual information. The main body individual information includes not only the information on the main body type but also information for identifying the ultrasonic diagnostic apparatus main body 2 such as a serial number. Thereby, the operator is able to know with which ultrasonic diagnostic apparatus main body 2 the ultrasonic probe 1 can communicate.

The operator can operate the operation unit 41 of the ultrasonic diagnostic apparatus main body 2 to request for establishment of wireless connection with the ultrasonic probe 1. In the case where the probe IDs of the plural ultrasonic probes 1 have been already acquired by the probe ID acquiring unit 47 and authenticated by the control unit 42, one of the ultrasonic probes 1 is selected by the selection operation of the operator, and the ultrasonic diagnostic apparatus main body 2 establishes the wireless connection with the selected ultrasonic probe 1. After the wireless connection is established, a drive instruction signal can be transmitted.

At step S15, the control unit 42 determines whether the drive instruction has been inputted or not by the operator. When the operator operates the operation unit 41 of the ultrasonic diagnostic apparatus main body 2 to input the drive instruction, the control unit 42 controls the communication control unit 32 to transmit the drive instruction signal from the wireless communication unit 31 to the authenticated ultrasonic probe 1. At step S16, the wireless communication unit 31 transmits the drive instruction signal to the authenticated ultrasonic probe 1.

When the wireless communication unit 17 of the ultrasonic probe 1 receives the drive instruction signal, the control unit 22 switches the condition, and thereby, the ultrasonic probe 1 turns from the standby condition to the normal operation condition. At step SP14, the ultrasonic probe 1 transmits and receives ultrasonic waves to generate the transfer signal based on the reception signals of the ultrasonic echoes. At step SP15, the control unit 22 controls the communication control unit 18 to transmit the transfer signal from the wireless communication unit 17 to the ultrasonic diagnostic apparatus main body 2.

At step S17, the wireless communication unit 31 of the ultrasonic diagnostic apparatus main body 2 receives the transfer signal. Thereby, the image forming unit 34 generates the ultrasonic image signal and the display unit 36 displays the ultrasonic diagnostic image.

In the above description, the case where the ultrasonic probe 1 operates in the standby condition and the normal operation condition has been explained, but the standby condition may not be provided and the ultrasonic probe 1 may operate only in the normal operation condition.

According to the wireless communication system ultrasonic diagnostic apparatus according to the embodiment, prior to establishing the wireless connection between the wireless communication unit 17 and the wireless communication unit 31, the probe ID is transmitted to the ultrasonic diagnostic apparatus main body 2 by using the probe ID transport unit 28 having a signal transport distance shorter than that of the wireless communication unit 17. Thereby, only combination of the ultrasonic probe 1 and the ultrasonic diagnostic apparatus main body 2 within a distance range, in which signal transmission by the probe ID transport unit 28 is possible, can be wirelessly connected. Accordingly, even in an environment in which plural ultrasonic probes and plural ultrasonic diagnostic apparatus main bodies can communicate with one another, a combination of a specific ultrasonic probe and a specific ultrasonic diagnostic apparatus main body to be used can be reliably determined by a simple operation. Therefore, false recognition of the pair can be prevented and the ultrasonic probes and the ultrasonic diagnostic apparatus main bodies can appropriately be connected.

Further, according to the wireless communication system ultrasonic diagnostic apparatus according to the embodiment, the ultrasonic probe 1 near to the ultrasonic diagnostic apparatus main body 2 is authenticated, and it can save wasted efforts for taking an ultrasonic probe far from the ultrasonic diagnostic apparatus main body 2 although there is the available ultrasonic probe nearby.

In addition, in the display unit 29b for displaying the authentication, not only the image display by a liquid crystal display device, but also light indication by an LED light, vibration or sound by a piezoelectric element, or the like may be used.

Next, an ultrasonic diagnostic apparatus according to the second embodiment of the present invention will be explained.

Figure 8:
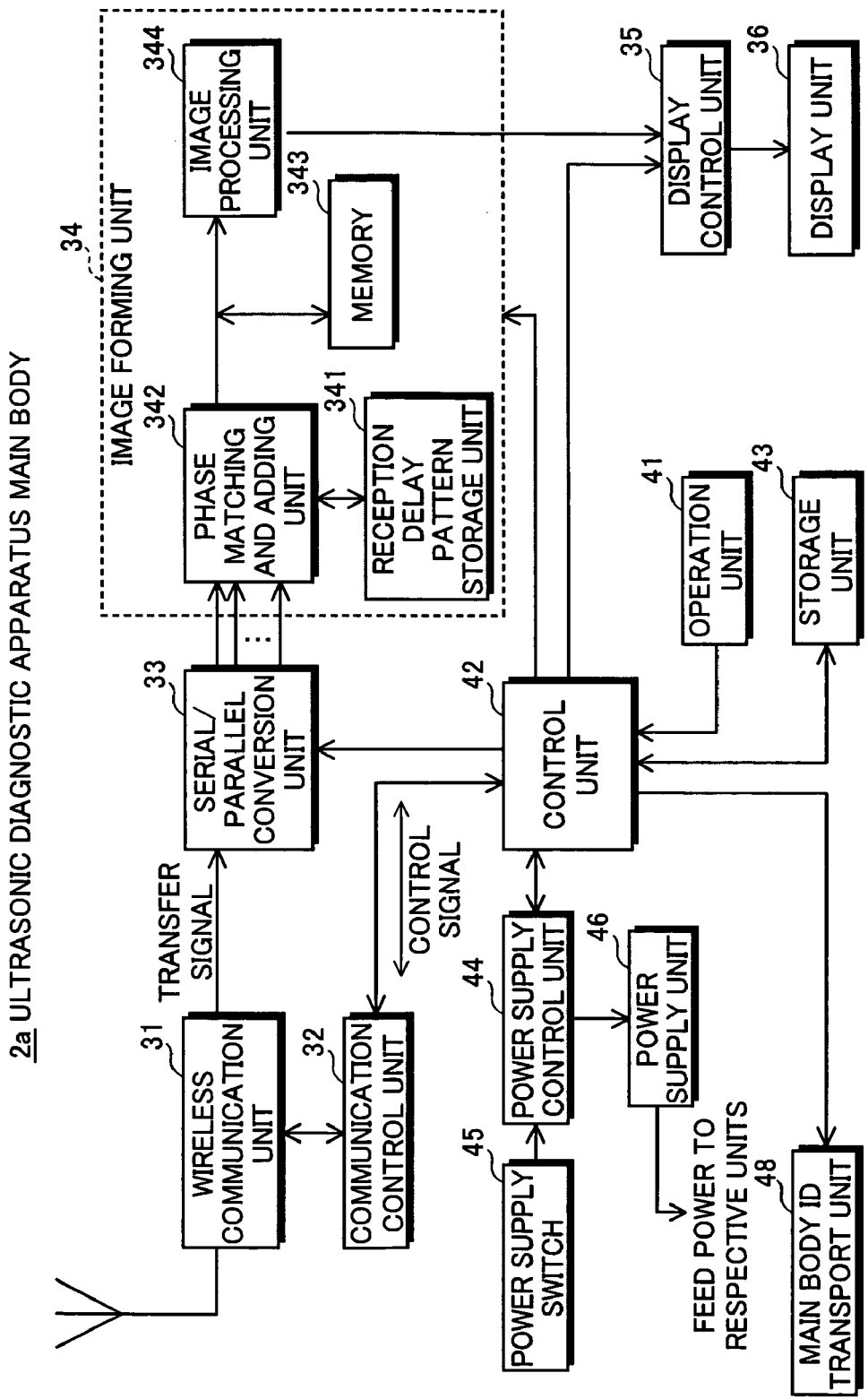
FIG. 8 is a block diagram showing a configuration of an ultrasonic diagnostic apparatus main body according to the second embodiment of the present invention.

FIG. 7 is a block diagram showing a configuration of an ultrasonic probe according to the second embodiment of the present invention, and FIG. 8 is a block diagram showing a configuration of an ultrasonic diagnostic apparatus main body according to the second embodiment of the present invention.

In the second embodiment, instead of performing authentication by using the probe ID, authentication is performed by using a main body ID unique to the ultrasonic diagnostic apparatus main body. For the purpose, a main body ID acquiring unit 30 as shown in FIG. 7 is provided in place of the probe ID transport unit 28 as shown in FIG. 2, and a main body ID transport unit 48 as shown in FIG. 8 is provided in place of the probe ID acquiring unit 47 as shown in FIG. 3.

In order to decide combination of an ultrasonic probe 1*a* and an ultrasonic diagnostic apparatus main body 2*a* prior to ultrasonic imaging, the main body ID transport unit 48 as shown in FIG. 8 receives the main body ID from the control unit 42, generates a transmission signal of the main body ID based thereon, and supplies the transmission signal to an antenna to transmit electric waves from the antenna, and thereby, transmits the main body ID. The main body ID transport unit 48 is formed to have a transport distance of the transmission signal shorter than that of the wireless communication unit 31. For example, in the case where the main body ID transport unit 48 is formed of a wireless transmitter as in the above-mentioned example, the transmission electric wave intensity of the main body ID transport unit 48 is set to a value weaker than the transmission electric wave intensity of the wireless communication unit 31. Alternatively, the main body ID transport unit 48 may be formed by printing a barcode or the like, and the main body ID may be read by an optical reading device. Further, transport means for RFID, infrared communication, or the like may be used as the main body ID transport unit 48.

The main body ID acquiring unit 30 as shown in FIG. 7 performs wireless communication with the main body ID transport unit 48 of the ultrasonic diagnostic apparatus main body 2*a* as shown in FIG. 8 to acquire the main body ID from the ultrasonic diagnostic apparatus main body 2*a*. The configuration of the main body ID acquiring unit 30 is not limited to a wireless receiver, but may be various configurations compliant to the transport system of the main body ID transport unit 48. For example, in the case where the main body ID transport unit 48 is formed by printing of a barcode or the like, the main body ID acquiring unit 30 is formed of an optical reading device. Alternatively, receiving means for RFID, infrared communication, or the like may be used as the main body ID acquiring unit 30.

Further, the main body ID acquiring unit 30 is not limited to a noncontact type, but may be a contact type. The main body ID acquiring unit 30 of a contact type may be formed to acquire an electric signal including the probe ID through an input terminal electrically connectable to an output terminal of the main body ID transport unit 48, or may be formed to read a shape unique to the ultrasonic probe and formed on the surface of the main body ID transport unit 48 by using a mechanical sensor or a pressure sensor.

As shown in the above-mentioned example, it is desirable that the main body ID acquiring unit 30 is suitable for reading information from a position extremely close thereto for reliable identification of the specific ultrasonic probe 1*a* and ultrasonic diagnostic apparatus main body 2*a*.

Figure 9:
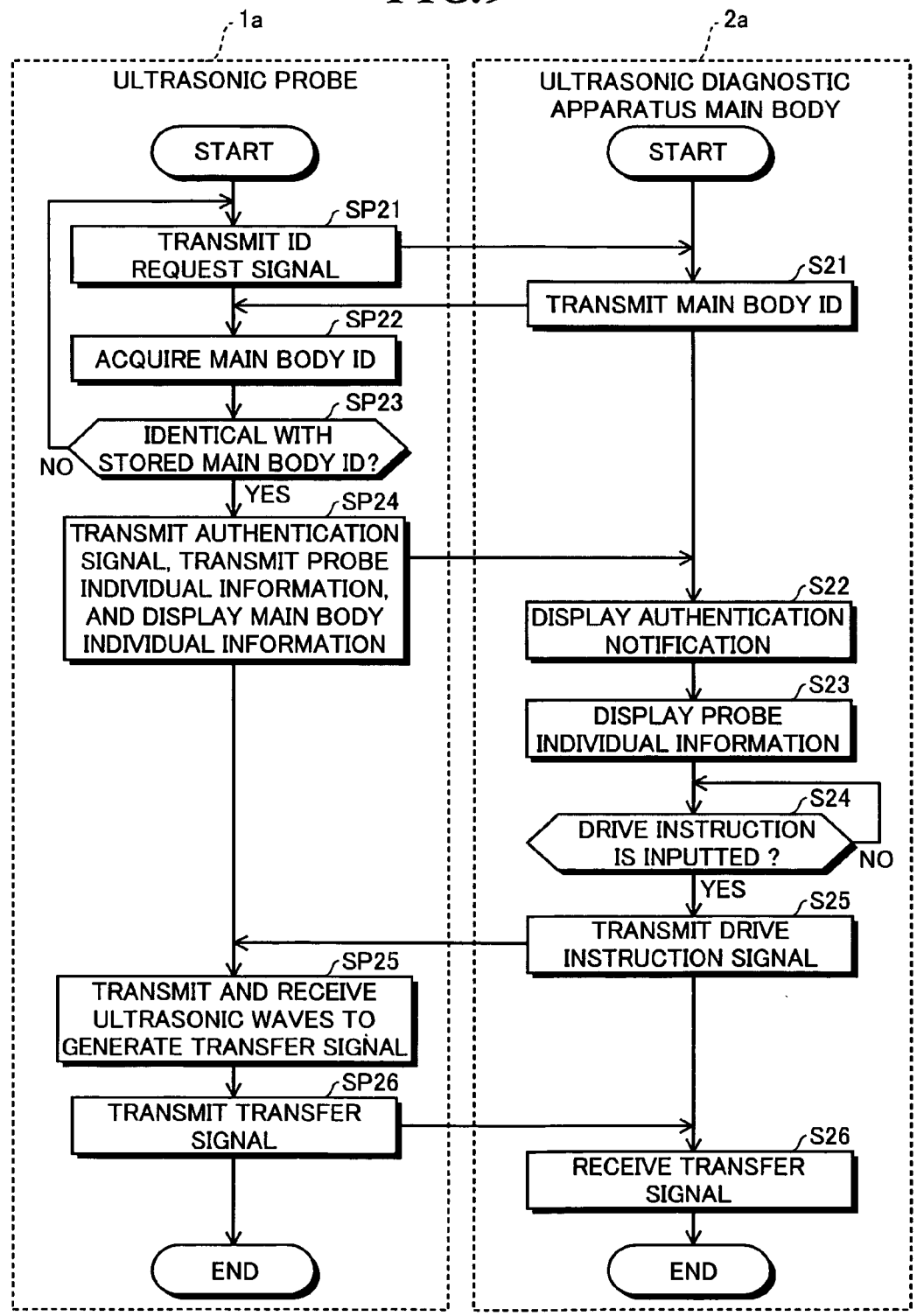
FIG. 9 is a flowchart for explanation of an operation example of an ultrasonic diagnostic apparatus according to the second embodiment of the present invention.

Next, an operation example of the ultrasonic diagnostic apparatus according to the second embodiment of the present invention will be explained by referring to FIGS. 7-9. FIG. 9 is a flowchart for explanation of the operation example of the ultrasonic diagnostic apparatus according to the second embodiment of the present invention. In FIG. 9, similarly to FIG. 5, the operation of the ultrasonic probe on the left side and the operation of the ultrasonic diagnostic apparatus main body on the right side are shown so that the interference relationship with each other is clear. Note that the power supply switch 45 of the ultrasonic diagnostic apparatus main body 2*a* is constantly in "ON" state.

In the process as shown in FIG. 9, the role of the ultrasonic probe 1 and the role of the ultrasonic diagnostic apparatus main body 2 in the process as shown in FIG. 5 are nearly reversed. That is, in the storage unit 43 of the ultrasonic diagnostic apparatus main body 2*a*, the main body ID unique to the ultrasonic diagnostic apparatus main body 2*a* is stored. Further, the display unit 36 of the ultrasonic diagnostic apparatus main body 2*a* has a function of a main body authentication notification unit for notifying reception of an authentication signal and a function of a probe information display unit for displaying probe individual information received from the ultrasonic probe.

On the other hand, the storage unit 23 of the ultrasonic probe 1*a* has a function of a main body ID storage unit for storing plural main body IDs. The control unit 22 has a function of a main body authentication unit for generating an authentication signal when the main body ID acquired by the main body ID acquiring unit 30 is identical with one of the plural main body IDs stored in the main body ID storage unit. The display unit 29*b* of the ultrasonic probe 1*a* has a function of a main body information display unit for displaying main body individual information of the ultrasonic main body having the main body ID acquired by the main body ID acquiring unit 30.

When the operator of the ultrasonic diagnostic apparatus turns on the power supply switch 25 of the ultrasonic probe 1*a*, the ultrasonic probe 1*a* transmits an ID request signal from the wireless communication unit 17 to the ultrasonic diagnostic apparatus main body 2*a* at step SP21, and turns to the standby condition.

When the wireless communication unit 31 of the ultrasonic diagnostic apparatus main body 2*a* receives the ID request signal, in response, the control unit 42 reads out the main body ID unique to the ultrasonic diagnostic apparatus main body 2*a* from the storage unit 43, and controls the main body ID transport unit 48 to transmit the main body ID signal representing the main body ID at step S21.

At step SP22, the main body ID acquiring unit 30 of the ultrasonic probe 1*a* by receives and demodulates the signal transmitted from the ultrasonic diagnostic apparatus main body 2*a* to acquire the main body ID, and outputs the main body ID to the control unit 22. At step SP23, the control unit 22 compares the main body ID acquired by the main body ID acquiring unit 30 with the main body IDs stored in the storage unit 23, and generates an authentication signal in the case where the main body ID acquired by the main body ID acquiring unit 30 is identical with one of the main body IDs stored in the storage unit 23. On the other hand, in the case where there is no identical main body ID in the storage unit 23, the process returns to step SP21, and the wireless communication unit 17 retransmits an ID request signal.

At step SP24, the control unit 22 controls the communication control unit 18 to transmit the authentication signal including the main body ID acquired by the main body ID acquiring unit 30 from the wireless communication unit 17.

Further, the control unit 22 reads out the probe individual information from the storage unit 23, and controls the communication control unit 18 to transmit the probe individual information from the wireless communication unit 17. Furthermore, the control unit 22 controls the display control unit 29a to allow the display unit 29b to display the authenticated main body ID or the corresponding main body individual information. Thereby, the operator is able to know with which ultrasonic probe 1a the ultrasonic diagnostic apparatus main body 2a can communicate.

The wireless communication unit 31 of the ultrasonic diagnostic apparatus main body 2a receives the authentication signal and the probe individual information transmitted from the ultrasonic probe 1a, and outputs the authentication signal and the probe individual information to the communication control unit 32. The communication control unit 32 detects the authentication signal and the probe individual information and outputs them to the control unit 42.

At step S22, the control unit 42 allows the display unit 36, via the display control unit 35, to display the authentication notification based on the received authentication signal. Thereby, the operator is able to know that the ultrasonic diagnostic apparatus main body 2a can communicate with the ultrasonic probe 1a. At step S23, the control unit 42 allows the display unit 36, via the display control unit 35, to display the probe individual information. Thereby, the operator is able to know with which ultrasonic probe 1a the ultrasonic diagnostic apparatus main body 2a can communicate.

The subsequent processes are the same as the process at the step S15 and the subsequent steps, and the process at the step SP14 and the subsequent steps in FIG. 5. That is, when the operator operates the operation unit 41 of the ultrasonic diagnostic apparatus main body 2a to input a drive instruction, the control unit 22 of the ultrasonic probe 1a switches the condition, and thereby, the ultrasonic probe 1 turns from the standby condition to the normal operation condition.

Figure 10:
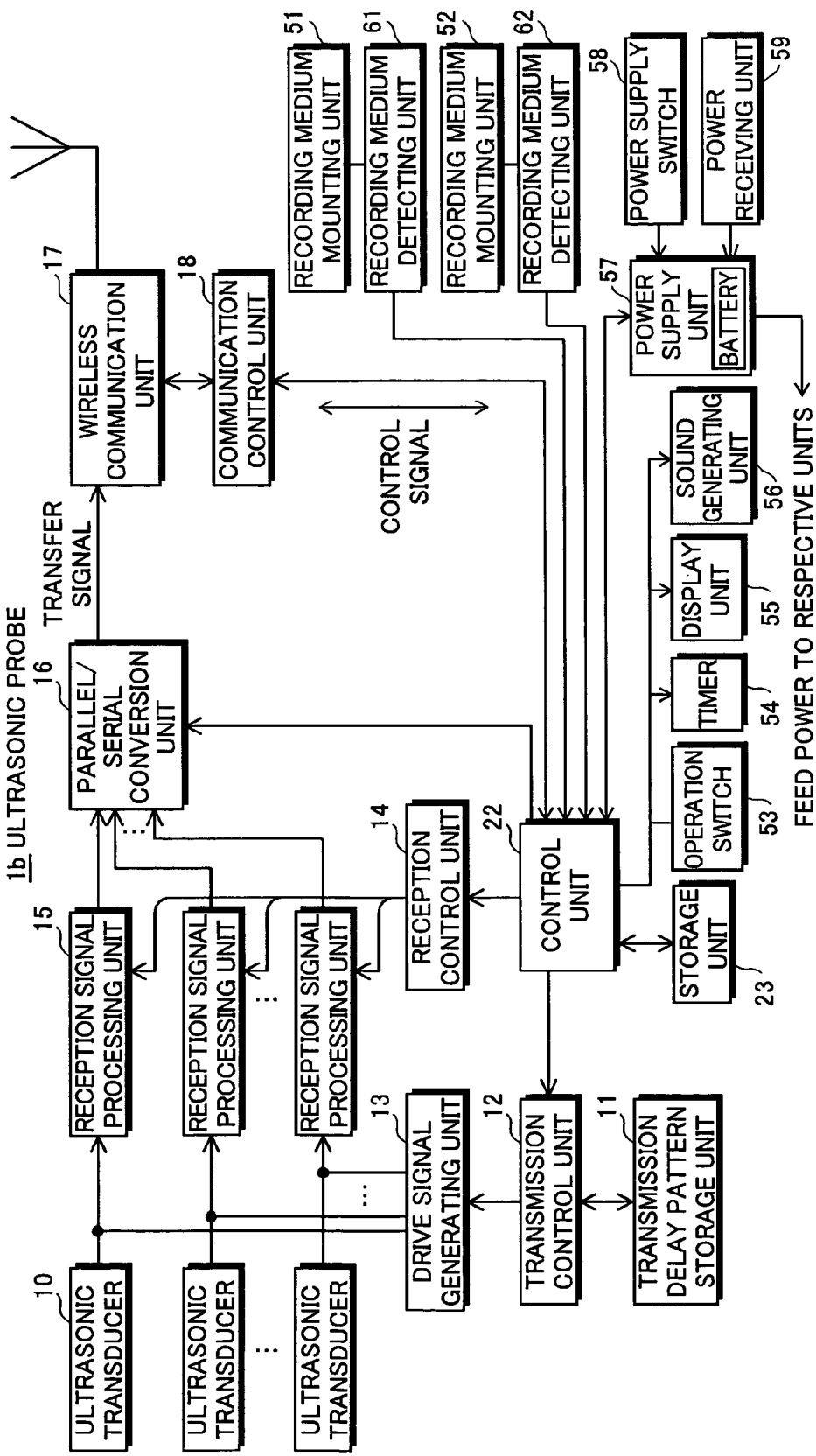
FIG. 10 is a block diagram showing a configuration of an ultrasonic probe according to the third embodiment of the present invention.
Figure 11:
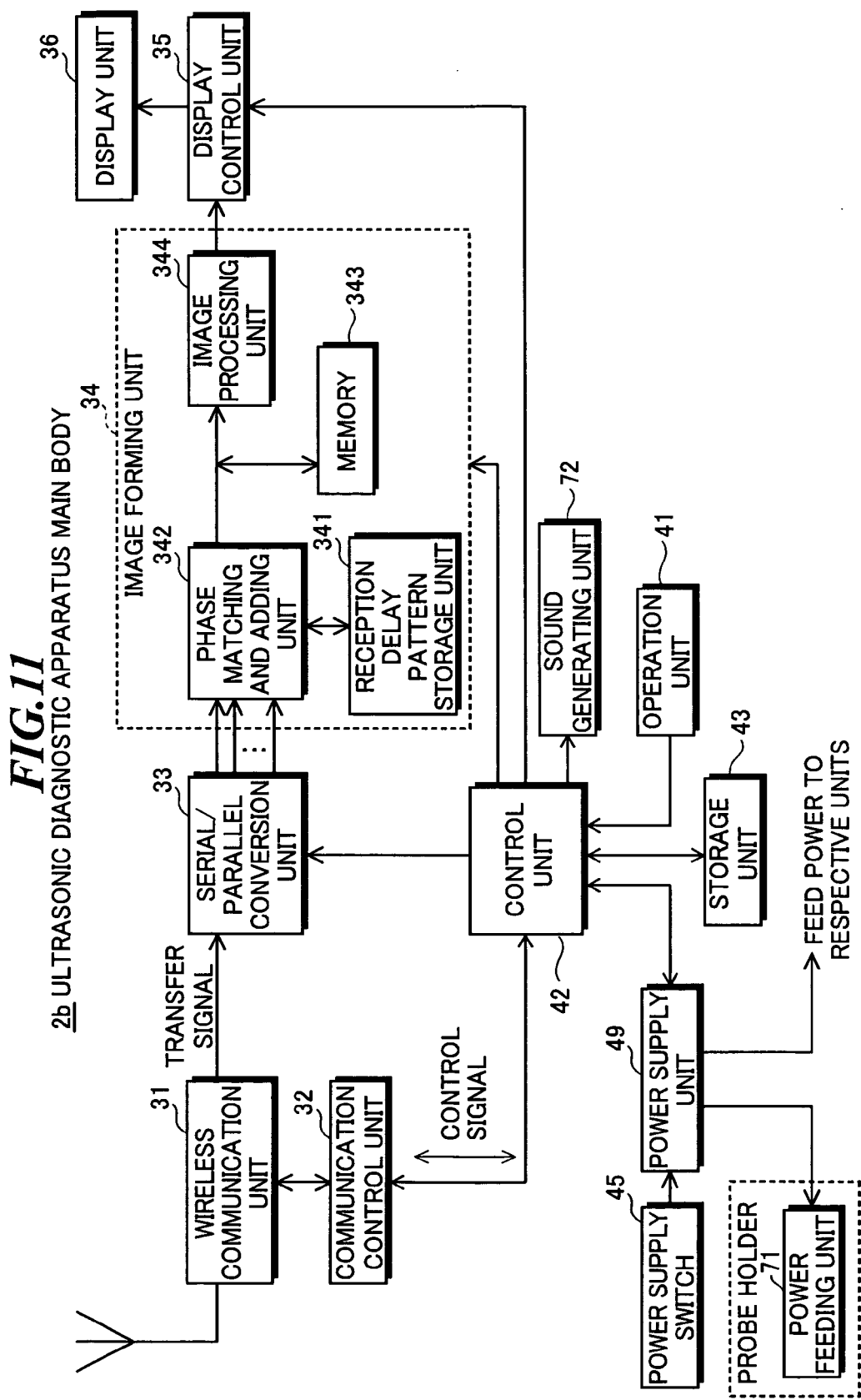
FIG. 11 is a block diagram showing a configuration of an ultrasonic diagnostic apparatus main body according to the third embodiment of the present invention.

Next, an ultrasonic diagnostic apparatus according to the third embodiment of the present invention will be explained. FIG. 10 is a block diagram showing a configuration of an ultrasonic probe according to the third embodiment of the present invention, and FIG. 11 is a block diagram showing a configuration of an ultrasonic diagnostic apparatus main body according to the third embodiment of the present invention. An ultrasonic diagnostic apparatus according to the third embodiment of the present invention includes an ultrasonic probe 1b as shown in FIG. 10 and an ultrasonic diagnostic apparatus main body 2b as shown in FIG. 11. The ultrasonic probe 1b may be an external probe of linear-scan type, convex-scan type, sector-scan type, or the like, or an ultrasonic endoscopic probe of radial-scan type or the like.

As shown in FIG. 10, the ultrasonic probe 1b includes plural ultrasonic transducers 10 forming a one-dimensional or two-dimensional transducer array, a transmission delay pattern storage unit 11, a transmission control unit 12, a drive signal generating unit 13, a reception control unit 14, plural channels of reception signal processing units 15, a parallel/serial conversion unit 16, a wireless communication unit 17, a communication control unit 18, a control unit 22, a storage unit 23, an operation switch 53, a timer 54, a display unit 55, a sound generating unit 56, a power supply unit 57 including a battery, a power supply switch 58, power receiving unit 59, at least one recording medium mounting unit (plural recording medium mounting units 51 and 52 are shown in FIG. 10), and at least one recording medium detecting unit (plural recording medium detecting units 61 and 62 are shown in FIG. 10).

The wireless communication unit 17 performs wireless communication with the ultrasonic diagnostic apparatus main body 2b, and thereby, transmits a transfer signal and so on to the ultrasonic diagnostic apparatus main body 2b, and receives various kinds of control signals from the ultrasonic diagnostic apparatus main body 2b to output the received signals to the communication control unit 18. The control unit 22 controls the respective units of the ultrasonic probe 1b according to the various kinds of control signals transmitted from the ultrasonic diagnostic apparatus main body 2b.

The operation switch 53 includes a switch for setting the ultrasonic diagnostic apparatus in a live mode or a freeze mode. The setting signal for the live mode or the freeze mode is included in the transmission signal together with the transfer signal and transmitted to the ultrasonic diagnostic apparatus main body 2b. Alternatively, the switching between the live mode and the freeze mode may be performed in the ultrasonic diagnostic apparatus main body 2b.

The power supply unit 57 supplies power to the respective units requiring power such as the signal processing unit 13, the reception signal processing units 15, the parallel/serial conversion unit 16, the wireless communication unit 17, the control unit 22, and so on based on the power of the battery. The ultrasonic probe 1b is provided with the power supply switch 58, and the power supply unit 57 controls whether the power is supplied to the respective units or not according to the status of the power supply switch 58. The battery can be charged by using the power receiving unit 59.

In the above-mentioned configuration, the plural ultrasonic transducers 10 to the storage unit 23, the timer 54, the power supply unit 57, the power receiving unit 59, the recording medium detecting units 61 and 62, and so on are accommodated in a casing. Further, in addition to the operation switch 53 and the power supply switch 58, a warning unit such as the display unit 55 including plural LEDs or the like or the sound generating unit 56 including a sound signal source, an amplifier, and a speaker is provided in the casing.

In the embodiment, the recording medium mounting units 51 and 52 each for mounting a recording medium in which ID information of examinees or operators has been recorded are provided in the ultrasonic probe 1b. The recording medium mounting units 51 and 52 have slots provided in the casing and the recording media can be inserted into the slots.

As the recording media, contact-type or non-contact type IC cards, magnetic cards, or the like in which ID information for identifying the examinees (patient) or operators (doctors) are used. For example, a patient registration card which records a patient ID number as a part of ordering information and is possessed by a patient, a patient registration card which records a patient ID number and is handed to a patient in a medical office, and an ID card which records ID information of a doctor and is possessed by the doctor are used.

When the power supply switch 58 is turned on, the power supply unit 57 supplies power at least to the control unit 22 and the recording medium detecting units 61 and 62. The recording medium detecting units 61 and 62 detect the mounting of the recording media in the recording medium mounting units 51 and 52 to activate detection signals, respectively. The control unit 22 controls the power supply unit 57 to start power supply to the drive signal generating unit 13, the reception signal processing units 15, the parallel/serial conversion unit 16, the wireless communication unit 17, and so on based on the detection results of the recording medium detecting units 61 and 62.

In the case where the plural recording medium mounting units 51 and 52 are provided as shown in FIG. 10, the control unit 22 controls the power supply unit 57 to start power supply to the drive signal generating unit 13 and so on when the recording medium detecting units 61 and 62 detect that the plural recording media are respectively mounted on the plural recording medium mounting units 51 and 52 or when the recording medium detecting unit 61 or 62 detects that at least one recording medium is mounted on the recording medium mounting unit 51 or 52.

For example, at least one kind of ID information is stored in the storage unit 23 in advance, and when the recording medium detecting unit 61 detects that the recording medium is mounted on the recording medium mounting unit 51, the recording medium detecting unit 61 reads the ID information recorded in the recording medium. The control unit 22 determines whether the ID information read by the recording medium detecting unit 61 and the ID information stored in the storage unit 23 are identical with each other or not, and controls the power supply unit 57 to start power supply to the drive signal generating unit 13 and so on in the case where they are determined to be identical with each other. Further, the control unit 22 controls the wireless communication unit 17, via the communication control unit 18, to transmit an imaging enable signal to the ultrasonic diagnostic apparatus main body 2b. The imaging enable signal represents that imaging has been ready at the ultrasonic probe 1b side and ultrasonic imaging has been enabled.

On the other hand, in the case where the control unit 22 determines that the ID information read by the recording medium detecting unit 61 and the ID information stored in the storage unit 23 are not identical with each other, the control unit 2 controls the warning unit (a first LED of the display unit 55 or the sound generating unit 56) to provide a notification that they are not identical with each other to the outside. Thereby, the first LED lights up or a first warning tone is emitted from the speaker, and the operator is able to recognize that both ID information are not identical with each other.

The timer 54 as a timing unit measures an elapsed time after the recording medium detecting unit 61 has detected the mounting of the recording medium on the recording medium mounting unit 51. When the time measured by the timer 54 exceeds a predetermined time, the control unit 22 controls the warning unit (a second LED of the display unit 55 or the sound generating unit 56) to provide a notification that the recording medium has been mounted on the recording medium mounting unit 51 to the outside. Thereby, the second LED lights up or a second warning tone is emitted from the speaker, and the operator is able to recognize that the predetermined time has elapsed after the mounting of the recording medium.

Further, the control unit 22 may supply a warning signal to the wireless communication unit 17 via the communication control unit 18 in addition or instead of the notification to the operator using the warning unit of the ultrasonic probe 1b. When the warning signal is supplied, the wireless communication unit 17 modulates a carrier signal based on the warning signal to generate a transmission signal and supplies the transmission signal to an antenna to transmit electric waves from the antenna, and thereby, transmits the warning signal to the ultrasonic diagnostic apparatus main body 2b.

When receiving the warning signal representing that the ID information read by the recording medium detecting unit 61 and the ID information stored in the storage unit 23 are not identical with each other, the control unit 42 of the ultrasonic diagnostic apparatus main body 2b as shown in FIG. 11 allows the display unit 36 to display a first warning or allows a sound generating unit 72 to generate a first warning tone. Further, when receiving the warning signal representing that the time measured by the timer 54 exceeds the predetermined time, the control unit 42 of the ultrasonic diagnostic apparatus main body 2b allows the display unit 36 to display a second warning or allows the sound generating unit 72 to generate a second warning tone.

Furthermore, when the time measured by the timer 54 exceeds the predetermined time, the control unit 22 controls the power supply unit 57 to stop power supply to the drive signal generating unit 13, the reception signal processing units 15, the parallel/serial conversion unit 16, the wireless communication unit 17, and so on. However, when the wireless communication unit 17 is in transmission, the control unit 22 controls the power supply unit 57 to stop power supply to the drive signal generating unit 13 and so on after the transmission is completed. Further, the control unit 22 controls the power supply unit 57 to stop power supply to the drive signal generating unit 13 and so on when the recording medium detecting unit 61 detects that the recording medium has been detached from the recording medium mounting unit 51.

On the other hand, referring to FIG. 11, the ultrasonic diagnostic apparatus main body 2b includes a wireless communication unit 31, a communication control unit 32, a serial/parallel conversion unit 33, an image forming unit 34, a display control unit 35, a display unit 36, an operation unit 41, a control unit 42, a storage unit 43, a power supply unit 49, a power supply switch 45, power feeding unit 71, and the sound generating unit 72.

The wireless communication unit 31 performs wireless communication with the ultrasonic probe 1b, and thereby, receives the transfer signal and the warning signal from the ultrasonic probe 1b and transmits various kinds of control signals to the ultrasonic probe 1b. The wireless communication unit 31 demodulates the signal received by an antenna to output serial sample data (transfer signal) representing the complex baseband signals obtained from the reception signals outputted from the plural ultrasonic transducers and output the warning signal.

The communication control unit 32 detects the warning signal outputted from the wireless communication unit 31 and outputs it to the control unit 42. The control unit 42 controls the display unit 36, via the display control unit 35, to perform warning display or controls the sound generating unit 72 to generate a warning tone.

The serial/parallel conversion unit 33 converts the serial sample data outputted from the wireless communication unit 31 into parallel sample data corresponding to the plural ultrasonic transducers. The image forming unit 34 generates an ultrasonic image signal as image information on tissues within the object, based on the parallel sample data outputted from the serial/parallel conversion unit 33.

The display control unit 35 allows the display unit 36 to display an ultrasonic diagnostic image based on the ultrasonic image signal generated by the image forming unit 34. The display unit 36 includes a display device such as an LCD, and displays the ultrasonic diagnostic image under the control of the display control unit 35.

The control unit 42 controls the respective units of the ultrasonic diagnostic apparatus according to the operation of an operator using the operation unit 41. The power supply switch 45 is provided in the ultrasonic diagnostic apparatus main body 2b, and the power supply unit 49 feeds power to the respective units according to the status of the power supply switch 45. The power feeding unit 71 provided in the probe holder feeds power to the power receiving unit 59 (FIG. 10) of the ultrasonic probe 1b by the electromagnetic action. The sound generating unit 72 includes a sound signal source, an amplifier, and a speaker, and generates a warning tone and so on under the control of the control unit 42.

Figure 12:
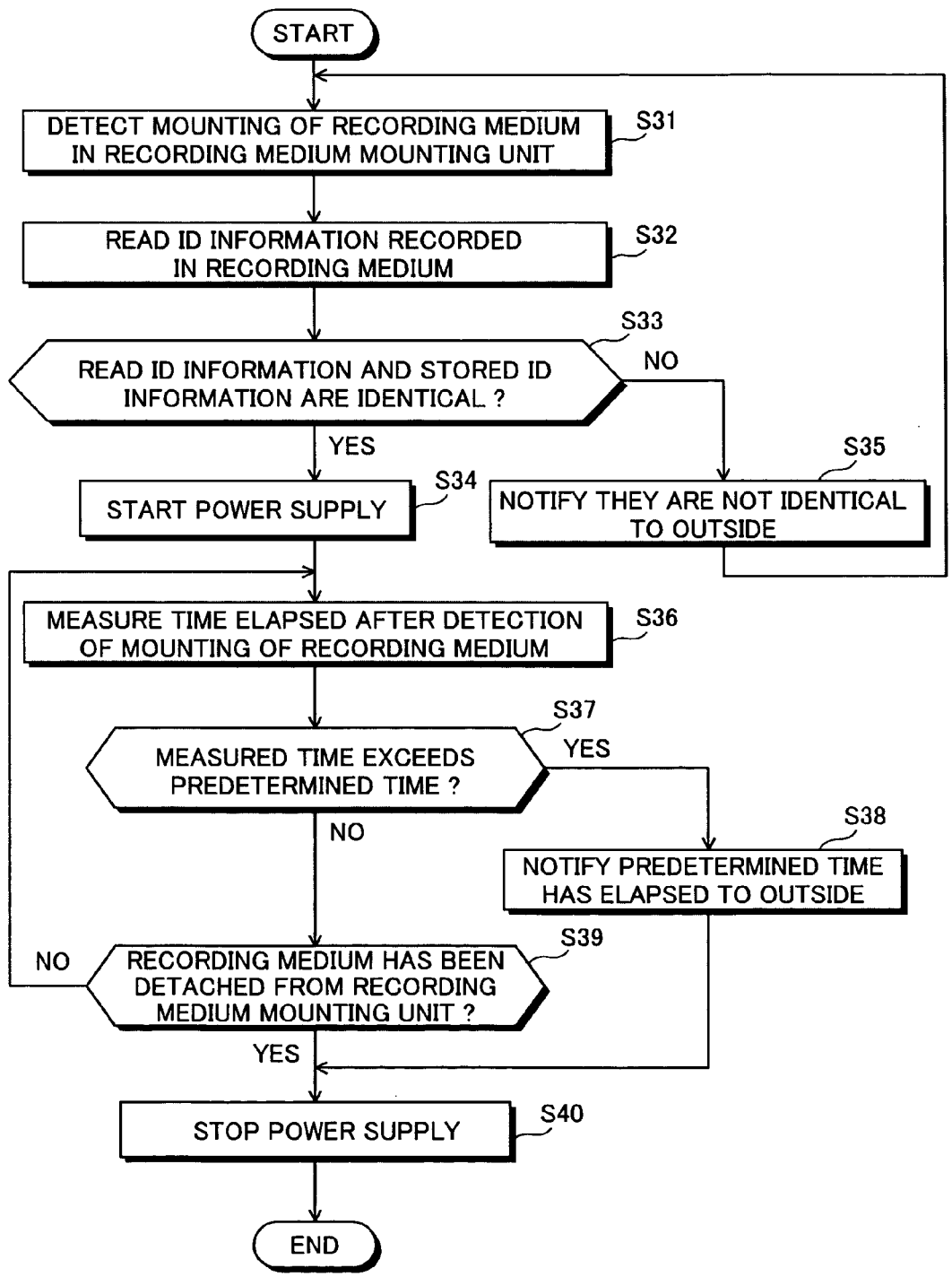
FIG. 12 is a flowchart for explanation of an operation example of the ultrasonic diagnostic apparatus according to the third embodiment of the present invention.

Next, an operation example of the ultrasonic probe according to the third embodiment of the present invention will be explained by referring to FIGS. 10 and 12. FIG. 12 is a flowchart for explanation of the operation example of the ultrasonic probe according to the third embodiment of the present invention.

At step S31, the recording medium detecting unit 61 detects the mounting of the recording medium on the recording medium mounting unit 51. At step S32, the recording medium detecting unit 61 reads the ID information recorded in the recording medium and output it to the control unit 22. At step S33, the control unit 22 determines whether the ID information read by the recording medium detecting unit 61 and the ID information stored in the storage unit 23 are identical with each other or not. In the case where they are identical with each other, the process moves to step S34, and, in the case where they are not identical with each other, the process moves to step S35.

At step S34, the control unit 22 controls the power supply unit 57 to start power supply to the drive signal generating unit 13, the reception signal processing units 15, the parallel/serial conversion unit 16, the wireless communication unit 17, and so on. Thereby, ultrasonic imaging using the ultrasonic probe 1b can be performed.

On the other hand, at step S35, the control unit 22 controls a first LED of the display unit 55 or the sound generating unit 56 to provide a notification that the ID information read by the recording medium detecting unit 61 and the ID information stored in the storage unit 23 are not identical with each other to the outside. Thereby, the first LED lights up or a first warning tone is emitted from the speaker, and the operator is able to recognize that both ID information are not identical with each other. Then, the process returns to step S31.

At step S36, the timer 54 measures an elapsed time after the recording medium detecting unit 61 has detected the mounting of the recording medium in the recording medium mounting unit 51. At step S37, the control unit 22 determines whether the time measured by the timer 54 exceeds a predetermined time or not. In the case where the measured time exceeds the predetermined time, the process moves to step S38, and in the case where the measured time does not exceed the predetermined time, the process moves to step S39.

At step S38, the control unit 22 controls a second LED of the display unit 55 or the sound generating unit 56 to provide a notification that the predetermined time has elapsed after the mounting of the recording medium to the outside. Thereby, the second LED lights up or a second warning tone is emitted from the speaker, and the operator is able to recognize that the predetermined time has elapsed after the mounting of the recording medium. Then, the process moves to step S40.

At step S39, the control unit 22 determines whether the recording medium detecting unit 61 has detected that the recording medium has been detached from the recording medium mounting unit 51 or not. In the case where the recording medium has not been detached, the process returns to step S36, and in the case where the recording medium has been detached, the process moves to step S40.

At step S40, the control unit 22 controls the power supply unit 57 to stop power supply to the drive signal generating unit 13, the reception signal processing units 15, the parallel/serial conversion unit 16, the wireless communication unit 17, and so on.

Next, an ultrasonic diagnostic apparatus according to the fourth embodiment of the present invention will be explained.

FIG. 13 is a block diagram showing a configuration of an ultrasonic probe according to the fourth embodiment of the present invention, and FIG. 14 is a block diagram showing a configuration of an ultrasonic diagnostic apparatus main body according to the fourth embodiment of the present invention. An ultrasonic diagnostic apparatus according to the fourth embodiment of the present invention includes an ultrasonic probe 1c as shown in FIG. 13 and an ultrasonic diagnostic apparatus main body 2c as shown in FIG. 14.

In the fourth embodiment, the detection signals and the ID information outputted from the recording medium detecting unit 61 of the ultrasonic probe 1c are transmitted to the ultrasonic diagnostic apparatus main body 2c, and control of the ultrasonic probe 1c is performed in the ultrasonic diagnostic apparatus main body 2c. The rest of the configuration is the same as that of the third embodiment.

The control unit 22 of the ultrasonic probe 1c outputs the detection signal and the ID information outputted from the recording medium detecting unit 61 to the wireless communication unit 17 via the communication control unit 18. The wireless communication unit 17 transmits the detection signal and the ID information to the ultrasonic diagnostic apparatus main body 2c. The wireless communication unit 31 of the ultrasonic diagnostic apparatus main body 2c receives the detection signal and the ID information and outputs them to the control unit 42 via the communication control unit 32.

The control unit 42 controls the communication control unit 32 to transmit the control signals to the ultrasonic probe 1c based on the detection result of the recording medium detecting unit 61. The control unit 22 of the ultrasonic probe 1c controls the power supply unit 57 to start power supply to the drive signal generating unit 13, the reception signal processing units 15, the parallel/serial conversion unit 16, the wireless communication unit 17, and so on according to the control signals transmitted from the ultrasonic diagnostic apparatus main body 2c.

For example, at least one kind of ID information is stored in the storage unit 43 in advance, and when the recording medium detecting unit 61 detects that the recording medium is mounted on the recording medium mounting unit 51, the recording medium detecting unit 61 reads the ID information recorded in the recording medium. The control unit 42 determines whether the ID information read by the recording medium detecting unit 61 and the ID information stored in the storage unit 43 are identical with each other or not, and controls the wireless communication unit 31 to transmit the control signals for starting power supply to the drive signal generating unit 13 and so on in the case where they are identical with each other. The wireless communication unit 17 of the ultrasonic probe 1c receives the control signals and outputs them to the control unit 22 via the communication control unit 18. The control unit 22 controls the power supply unit 57 to start power supply to the drive signal generating unit 13 and so on.

On the other hand, in the case where the ID information read by the recording medium detecting unit 61 and the ID information stored in the storage unit 23 are determined to be not identical with each other, the control unit 42 controls the wireless communication unit 31 to transmit a warning signal for warning that they are not identical with each other. The wireless communication unit 17 of the ultrasonic probe 1c receives the warning signal and outputs it to the control unit 22 via the communication control unit 18. The control unit 22 controls the warning unit (a first LED of the display unit 55 or the sound generating unit 56) to provide a notification that they are not identical with each other to the outside. Thereby, the first LED lights up or a first warning tone is emitted from a speaker, and the operator is able to recognize that both ID information are not identical with each other.

In the ultrasonic diagnostic apparatus main body 2c, a timer 73 as a timing unit measures an elapsed time after the recording medium detecting unit 61 has detected the mounting of the recording medium in the recording medium mounting unit 51. In the case where the time measured by the timer 73 exceeds a predetermined time, the control unit 42 controls the wireless communication unit 31 to transmit a warning signal for warning that the recording medium is mounted on the recording medium mounting unit 51. The wireless communication unit 17 of the ultrasonic probe 1c receives the warning signal and outputs it to the control unit 22 via the communication control unit 18. The control unit 22 controls the warning unit (a second LED of the display unit 55 or the sound generating unit 56) to provide a notification that they are not identical with each other to the outside. Thereby, the second LED lights up or a second warning tone is emitted from the speaker, and the operator is able to recognize that a predetermined time has been elapsed after the recording medium is mounted.

Further, the control unit 42 may control the display unit 36 or the sound generating unit 72 to emit warning in addition or instead of the notification to the operator using the warning unit of the ultrasonic probe 1c.

Furthermore, when the time measured by the timer 73 exceeds the predetermined time, the control unit 42 controls the wireless communication unit 31 to transmit a control signal for stopping power supply to the drive signal generating unit 13, the reception signal processing units 15, the parallel/serial conversion unit 16, the wireless communication unit 17, and so on. The wireless communication unit 17 of the ultrasonic probe 1c receives the control signal and outputs it to the control unit 22 via the communication control unit 18. The control unit 22 controls the power supply unit 57 to stop power supply to the drive signal generating unit 13 and so on. However, when the wireless communication unit 17 is in transmission, the control unit 22 controls the power supply unit 57 to stop power supply to the drive signal generating unit 13 and so on after the transmission of the transfer signal is completed.

The invention claimed is:

1. An ultrasonic diagnostic apparatus comprising:
an ultrasonic probe including plural ultrasonic transducers configured to transmit ultrasonic waves according to drive signals, and receive ultrasonic echoes to output reception signals, a signal processing unit configured to perform signal processing on the reception signals outputted from said plural ultrasonic transducers to generate a transfer signal, and a first wireless communication unit configured to transmit the transfer signal to an outside via wireless communication; and
an ultrasonic diagnostic apparatus main body including a second wireless communication unit configured to receive the transfer signal transmitted from said first wireless communication unit, and an image signal generating unit configured to generate an image signal based on the transfer signal received by said second wireless communication unit;
wherein said ultrasonic probe further includes a probe ID transport unit having a transport distance shorter than that of said first wireless communication unit, and configured to transport a probe ID for identifying said ultrasonic probe to an outside of said ultrasonic probe in a noncontact manner, and said probe ID transport unit includes one of a wireless transmitter, an RFID (radio frequency identification) unit, and an infrared communication unit;
said ultrasonic diagnostic apparatus main body further includes a probe ID acquiring unit configured to acquire the probe ID transported from said probe ID transport unit, a storage unit configured to store plural probe IDs, and a control unit configured to establish, when the probe ID acquired by said probe ID acquiring unit is identical with one of the plural probe IDs stored in said storage unit, wireless connection between an ultrasonic probe having the probe ID acquired by said probe ID acquiring unit and said ultrasonic diagnostic apparatus main body; and
said second wireless communication unit is configured to receive the transfer signal from said ultrasonic probe having the probe ID acquired by said probe ID acquiring unit.

2. The ultrasonic diagnostic apparatus according to claim 1, wherein:
said second wireless communication unit is configured to transmit a drive instruction signal, which instructs driving of said plural ultrasonic transducers, to said ultrasonic probe having the probe ID acquired by said probe ID acquiring unit; and
said ultrasonic probe is configured to drive said plural ultrasonic transducers according to the drive instruction signal.

3. The ultrasonic diagnostic apparatus according to claim 1, wherein:
said control unit is configured to generate an authentication signal when the probe ID acquired by said probe ID acquiring unit is identical with one of the plural probe IDs stored in said storage unit; and
said second wireless communication unit is configured to receive the transfer signal transmitted from an ultrasonic probe having the probe ID authenticated by said control unit.

4. The ultrasonic diagnostic apparatus according to claim 3, wherein:
said ultrasonic diagnostic apparatus main body transmits the authentication signal to said ultrasonic probe having the probe ID authenticated by said control unit; and
said ultrasonic probe further includes a probe authentication notification unit configured to provide a notification of authentication by using at least one of light, sound, and vibration when the authentication signal is received.

5. The ultrasonic diagnostic apparatus according to claim 1, wherein said ultrasonic diagnostic apparatus main body further includes a probe information display unit configured to display probe individual information of said ultrasonic probe having the probe ID acquired by said probe ID acquiring unit.

6. The ultrasonic diagnostic apparatus according to claim 1, wherein:
said ultrasonic diagnostic apparatus main body is configured to transmit main body individual information of said ultrasonic diagnostic apparatus main body to said ultrasonic probe having the probe ID acquired by said probe ID acquiring unit; and
said ultrasonic probe further includes a main body information display unit configured to display the main body individual information received from said ultrasonic diagnostic apparatus main body.

7. An ultrasonic diagnostic apparatus comprising:
an ultrasonic probe including plural ultrasonic transducers configured to transmit ultrasonic waves according to drive signals, and receive ultrasonic echoes to output reception signals, a signal processing unit configured to perform signal processing on the reception signals outputted from said plural ultrasonic transducers to generate a transfer signal, and a first wireless communication unit configured to transmit the transfer signal to an outside via wireless communication; and an ultrasonic diagnostic apparatus main body including a second wireless communication unit configured to receive the transfer signal transmitted from said first wireless communication unit, and an image signal generating unit configured to generate an image signal based on the transfer signal received by said second wireless communication unit;

wherein said ultrasonic diagnostic apparatus main body further includes a main body ID transport unit having a transport distance shorter than that of said first wireless communication unit, and configured to transport a main body ID for identifying said ultrasonic diagnostic apparatus main body to an outside of said ultrasonic diagnostic apparatus main body in a noncontact manner, and said main body ID transport unit includes one of a wireless transmitter, an RFID (radio frequency identification) unit, and an infrared communication unit;

said ultrasonic probe further includes a main body ID acquiring unit configured to acquire the main body ID transported from said main body ID transport unit, a storage unit configured to store plural main body IDs, and a control unit configured to establish, when the main body ID acquired by said main body ID acquiring unit is identical with one of the plural main body IDs stored in said storage unit, wireless connection between said ultrasonic probe and an ultrasonic diagnostic apparatus main body having the main body ID acquired by said main body ID acquiring unit; and said first wireless communication unit is configured to transmit the transfer signal to said ultrasonic diagnostic apparatus main body having the main body ID acquired by said main body ID acquiring unit.

8. The ultrasonic diagnostic apparatus according to claim 7, wherein said ultrasonic probe is configured to drive, when said main body ID acquiring unit acquires the main body ID, said plural ultrasonic transducers according to a drive instruction signal transmitted from said ultrasonic diagnostic apparatus main body.

9. The ultrasonic diagnostic apparatus according to claim 7, wherein:

said control unit is configured to generate an authentication signal when the main body ID acquired by said main body ID acquiring unit is identical with one of the plural main body IDs stored in said main body ID storage unit; and said first wireless communication unit is configured to transmit the transfer signal to an ultrasonic diagnostic apparatus main body having the main body ID authenticated by said main body authentication unit.

10. The ultrasonic diagnostic apparatus according to claim 9, wherein:

said ultrasonic probe is configured to transmit the authentication signal to said ultrasonic diagnostic apparatus main body having the main body ID authenticated by said main body authentication unit; and said ultrasonic diagnostic apparatus main body further includes a main body authentication notification unit configured to provide a notification of authentication by using at least one of light, sound, and vibration when the authentication signal is received.

11. The ultrasonic diagnostic apparatus according to claim 7, wherein said ultrasonic probe further includes a main body information display unit configured to display main body individual information of said ultrasonic diagnostic apparatus main body having the main body ID acquired by said main body ID acquiring unit.

12. The ultrasonic diagnostic apparatus according to claim 7, wherein:

said ultrasonic probe is configured to transmit probe individual information of said ultrasonic probe to said ultrasonic diagnostic apparatus main body having the main body ID acquired by said main body ID acquiring unit; and said ultrasonic diagnostic apparatus main body further includes a main body information display unit configured to display the probe individual information received from said ultrasonic probe.

13. An ultrasonic diagnostic apparatus comprising:

an ultrasonic probe including a recording medium mounting unit configured to mount a recording medium in which ID information of one of an examinee and an operator has been recorded, a recording medium detecting unit configured to detect mounting of the recording medium on said recording medium mounting unit and read, when detecting the mounting of the recording medium on said recording medium mounting unit, the ID information recorded in said recording medium, plural ultrasonic transducers configured to transmit ultrasonic waves according to drive signals, and receive ultrasonic echoes to output reception signals, a signal processing unit configured to perform signal processing on the reception signals outputted from said plural ultrasonic transducers to generate a transfer signal, a wireless communication unit configured to transmit the ID information read by said recording medium detecting unit and the transfer signal generated by said signal processing unit to an outside via wireless communication, a power supply unit including a battery and configured to supply power to respective units requiring power, and a control unit configured to control at least said power supply unit; and an ultrasonic diagnostic apparatus main body configured to perform wireless communication with said ultrasonic probe, and generate an image signal based on the transfer signal transmitted from said ultrasonic probe, said ultrasonic diagnostic apparatus main body including a storage unit configured to store at least one kind of ID information, and a second control unit configured to determine whether the ID information read by said recording medium detecting unit and the ID information stored in said storage unit are identical or not, and control at least said power supply unit via said control unit to start ultrasonic imaging in the case where they are identical with each other.

14. The ultrasonic diagnostic apparatus according to claim 13, wherein said ultrasonic probe further includes a warning unit configured to provide, in the case where the ID information read by said recording medium detecting unit and the ID information stored in said storage unit are not identical with each other, a notification that they are not identical with each other to an outside.

15. An ultrasonic probe comprising:

plural ultrasonic transducers configured to transmit ultrasonic waves according to drive signals, and receiving ultrasonic echoes to output reception signals;

a signal processing unit configured to perform signal processing on the reception signals outputted from said plural ultrasonic transducers to generate a transfer signal;

a wireless communication unit configured to transmit the transfer signal generated by said signal processing unit to an outside via wireless communication;

a recording medium mounting unit configured to mount a recording medium in which ID information of one of an examinee and an operator has been recorded;

a recording medium detecting unit configured to detect mounting of the recording medium on said recording medium mounting unit and read, when detecting the mounting of the recording medium on said recording medium mounting unit, the ID information recorded in said recording medium;

a storage unit configured to store at least one kind of ID information;

a power supply unit including a battery and configured to supply power to respective units requiring power; and a control unit configured to determine whether the ID information read by said recording medium detecting unit and the ID information stored in said storage unit are identical or not, and control at least said power supply unit to start ultrasonic imaging in the case where they are identical with each other.

16. The ultrasonic probe according to claim 15, wherein said ultrasonic probe further includes a warning unit configured to provide, in the case the ID information read by said recording medium detecting unit and the ID information stored in said storage unit are not identical with each other, a notification that they are not identical with each other to an outside.

17. The ultrasonic probe according to claim 15, further comprising:

a timing unit configured to measure a time elapsed after said recording medium detecting unit detects the mounting of said recording medium on said recording medium mounting unit; and a warning unit configured to provide a notification that said recording medium is mounted on said recording medium mounting unit to an outside when the time measured by said timing unit exceeds a predetermined time.

18. The ultrasonic probe according to claim 17, wherein said control unit is configured to control said power supply unit to stop power supply when the time measured by said timer exceeds the predetermined time.

19. The ultrasonic probe according to claim 15, wherein said control unit is configured to control said power supply unit to stop power supply when said recording medium detecting unit detects that said recording medium is detached from said recording medium mounting unit.

20. The ultrasonic probe according to claim 15, comprising plural recording medium mounting units;

wherein said control unit is configured to control said power supply unit to start power supply when said recording medium detecting unit detects that at least one recording medium is mounted on at least one of said plural recording medium mounting units.

21. The ultrasonic probe according to claim 15, further comprising:

a casing configured to accommodate at least said plural ultrasonic transducers, said signal processing unit, said wireless communication unit, said power supply unit, and said control unit;

wherein said recording medium mounting unit has a slot provided in said casing, and said recording medium includes one of an IC card and a magnetic card which is capable of being inserted into said slot, and in which ID information for identifying one of an examinee and an operator has been recorded.

* * * * *